United States Patent
Thomas et al.

(10) Patent No.: US 11,043,289 B2
(45) Date of Patent: Jun. 22, 2021

(54) MONITORING, PREDICTING AND ALERTING FOR CENSUS PERIODS IN MEDICAL INPATIENT UNITS

(71) Applicant: General Electric Company, Schenectady, NY (US)

(72) Inventors: Bex George Thomas, Laguna Nigel, CA (US); Rajesh Tyagi, Niskayuna, NY (US); Nitish Umang, Schenectady, NY (US); Aristotelis Emmanouil Thanos Filis, Schenectady, NY (US); Andrew Day, Newtown, PA (US); Savanoor Pradeep Rai, Naperville, IL (US)

(73) Assignee: General Electric Company, Schenectady, NY (US)

( * ) Notice: Subject to any disclaimer, the term of this patent is extended or adjusted under 35 U.S.C. 154(b) by 131 days.

(21) Appl. No.: 16/366,247

(22) Filed: Mar. 27, 2019

(65) Prior Publication Data

US 2020/0312430 A1 Oct. 1, 2020

(51) Int. Cl.
*G16H 40/20* (2018.01)
*G16H 10/60* (2018.01)
(Continued)

(52) U.S. Cl.
CPC ........... *G16H 10/60* (2018.01); *G06N 3/08* (2013.01); *G16H 15/00* (2018.01); *G16H 50/30* (2018.01);
(Continued)

(58) Field of Classification Search
CPC ........ G16H 40/20; G16H 10/60; G16H 40/63; G16H 70/20; G16H 40/40; G16H 40/00
See application file for complete search history.

(56) References Cited

U.S. PATENT DOCUMENTS 9,311,449 B2    4/2016  Levin et al.
2012/0191465 A1  7/2012  Xue et al.
(Continued)

FOREIGN PATENT DOCUMENTS

WO    WO-2011026098 A2 *  3/2011  ..... G06Q 10/063114

OTHER PUBLICATIONS

Hong, Woo Suk, Adrian Daniel Haimovich, and R. Andrew Taylor. "Predicting hospital admission at emergency department triage using machine learning." PloS one 13.7 (2018): e0201016. (Year: 2018).*

(Continued)

*Primary Examiner* — Elaine Gort
*Assistant Examiner* — Constantine B Siozopoulos
(74) *Attorney, Agent, or Firm* — Amin, Turocy & Watson, LLP

(57) ABSTRACT

Systems and techniques for monitoring, predicting and/or alerting for census periods in medical inpatient units are presented. A system can perform a first machine learning process to learn patterns in patient flow data related to a set of patient identities and a set of operations associated with a set of medical inpatient units. The system can also perform a second machine learning process to detect abnormalities associated with the patterns in the patient flow data. Furthermore, the system can determine patient census data associated with a prediction for a total number of patient identities in the set of medical inpatient units during a period of time based on the patterns and the abnormalities. The system can also generate an alert for a user interface in response to a determination that the patient census data satisfies a defined criterion.

20 Claims, 11 Drawing Sheets

(51) Int. Cl.
- *G16H 15/00* (2018.01)
- *G16H 50/30* (2018.01)
- *G06N 3/08* (2006.01)
- G16H 50/20 (2018.01)
- G16H 40/63 (2018.01)
- G06N 3/04 (2006.01)

(52) U.S. Cl.
CPC ......... *G06N 3/0445* (2013.01); *G06N 3/0454* (2013.01); *G16H 40/63* (2018.01); *G16H 50/20* (2018.01)

(56) References Cited

U.S. PATENT DOCUMENTS

| | | | |
|---|---|---|---|
| 2014/0108033 A1* | 4/2014 | Akbay | G16H 40/20 |
| | | | 705/2 |
| 2014/0278528 A1 | 9/2014 | Simha et al. | |
| 2019/0180868 A1* | 6/2019 | Makram | G06Q 10/0631 |
| 2019/0304596 A1* | 10/2019 | Padala | G06Q 10/06375 |

OTHER PUBLICATIONS

European search report received for European Patent Application serial No. 20164356.6 dated Aug. 17, 2020, 9 Pages.

\* cited by examiner

MONITORING, PREDICTING AND ALERTING FOR CENSUS PERIODS IN MEDICAL INPATIENT UNITS

TECHNICAL FIELD

This disclosure relates generally to adaptive learning systems (e.g., via employment of machine learning).

BACKGROUND

Data related to a hospital generally resides in different digital systems, is generated at various frequencies with respect to time, and/or employs a variety of different technologies. For instance, a vast amount of data is generally generated daily by various network-connected medical devices and/or network-connected medical systems (e.g., medical devices, medical equipment, sensors, mobile devices, controllers, medical logs, etc.) in a hospital environment. In certain instances, such data can be saved on cloud-based data infrastructure and can be stored as unstructured data. Consequently, processing, searching and/or analyzing the voluminous amounts of unstructured data associated with a hospital environment is computationally expensive. Furthermore, gleaning insights from data stored on a cloud-based data infrastructure associated with a hospital environment is generally time consuming and/or not easy to achieve.

SUMMARY

The following presents a simplified summary of the specification in order to provide a basic understanding of some aspects of the specification. This summary is not an extensive overview of the specification. It is intended to neither identify key or critical elements of the specification, nor delineate any scope of the particular implementations of the specification or any scope of the claims. Its sole purpose is to present some concepts of the specification in a simplified form as a prelude to the more detailed description that is presented later.

According to an embodiment, a system includes a patient flow component, a monitoring engine component, a patient census component, and an alert component. The patient flow component can perform a first machine learning process to learn one or more patterns in patient flow data related to a set of patient identities and a set of operations associated with a set of medical inpatient units. The monitoring engine component can monitor the one or more patterns in the patient flow data. The monitoring engine can also perform a second machine learning process to detect one or more abnormalities associated with the one or more patterns in the patient flow data. The patient census component can determine patient census data associated with a prediction for a total number of patient identities in the set of medical inpatient units during a period of time based on the one or more patterns and the one or more abnormalities. The alert component can generate an alert for a user interface in response to a determination that the patient census data satisfies a defined criterion. In certain embodiments, the patient census component can include a real time component and/or a learning/prediction component to facilitate determining patient census data.

According to another embodiment, a method is provided. The method comprises performing, by a system comprising a processor, a first machine learning process to learn one or more patterns in patient flow data related to a set of patient identities and a set of operations associated with a set of medical inpatient units. The method also comprises monitoring, by the system, the one or more patterns in the patient flow data. Furthermore, the method comprises performing, by the system, a second machine learning process to detect one or more abnormalities associated with the one or more patterns in the patient flow data. The method also comprises determining, by the system, patient census data associated with a prediction for a total number of patient identities in the set of medical inpatient units during a period of time based on the one or more patterns and the one or more abnormalities.

According to yet another embodiment, a computer readable storage device is provided. The computer readable storage device comprises instructions that, in response to execution, cause a system comprising a processor to perform operations, comprising: performing a machine learning process to learn one or more patterns in patient flow data related to a set of patient identities and a set of operations associated with a set of medical inpatient units, monitoring the one or more patterns in the patient flow data, determining patient census data associated with a prediction for a total number of patient identities in the set of medical inpatient units during a period of time based on the one or more patterns, and generating one or more alerts for a user interface in response to a determination that the patient census data satisfies a defined criterion.

The following description and the annexed drawings set forth certain illustrative aspects of the specification. These aspects are indicative, however, of but a few of the various ways in which the principles of the specification may be employed. Other advantages and novel features of the specification will become apparent from the following detailed description of the specification when considered in conjunction with the drawings.

BRIEF DESCRIPTION OF THE DRAWINGS

Numerous aspects, implementations, objects and advantages of the present invention will be apparent upon consideration of the following detailed description, taken in conjunction with the accompanying drawings, in which like reference characters refer to like parts throughout, and in which.

DETAILED DESCRIPTION

Figure 1:
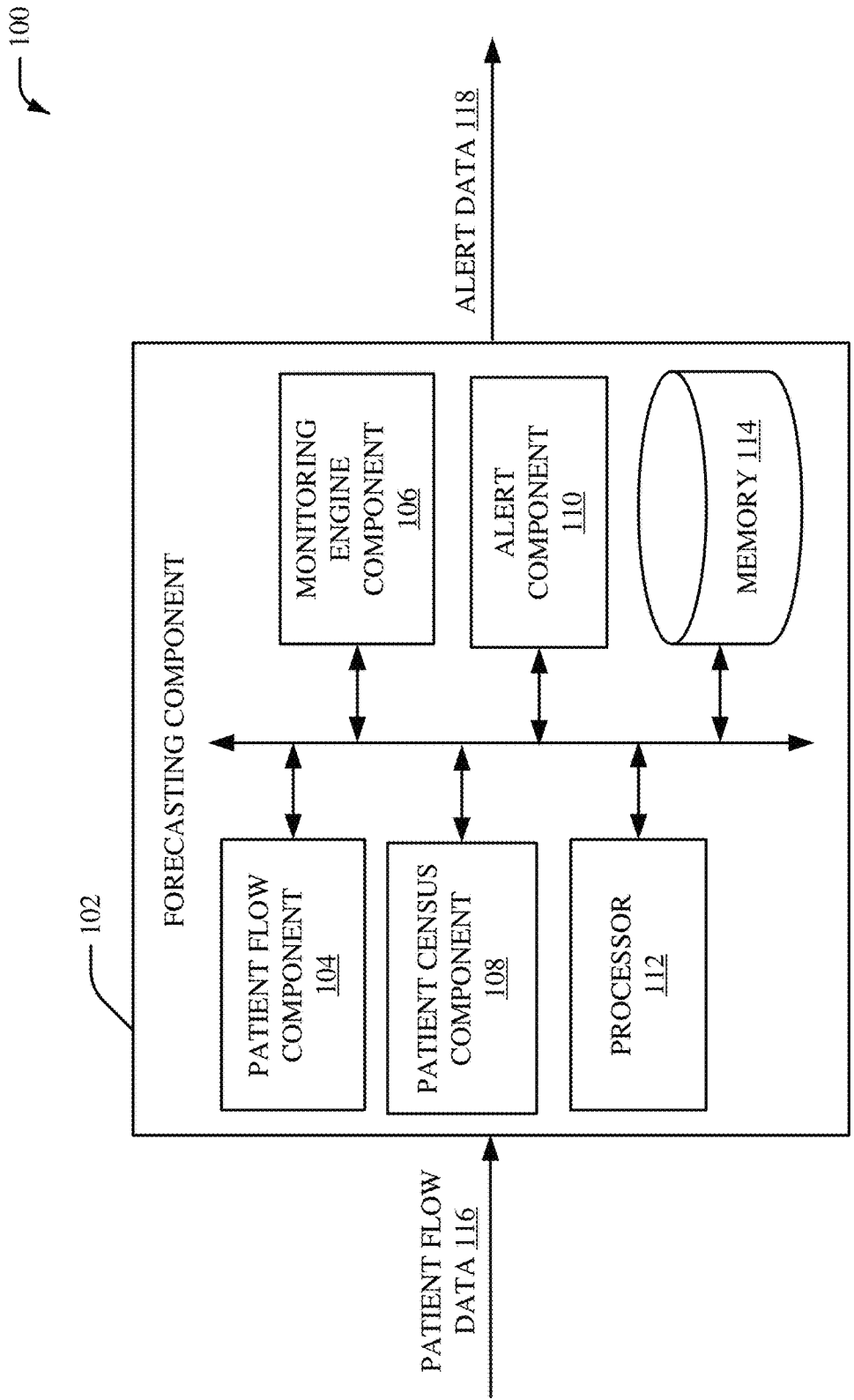
FIG. 1 illustrates a high-level block diagram of an example forecasting component, in accordance with one or more embodiments described herein.

Various aspects of this disclosure are now described with reference to the drawings, wherein like reference numerals are used to refer to like elements throughout. In the following description, for purposes of explanation, numerous specific details are set forth in order to provide a thorough understanding of one or more aspects. It should be understood, however, that certain aspects of this disclosure may be practiced without these specific details, or with other methods, components, materials, etc. In other instances, well-known structures and devices are shown in block diagram form to facilitate describing one or more aspects.

Systems and techniques for monitoring, predicting and/or alerting for census periods in medical inpatient units are presented. For instance, an adaptive learning system that monitors, predicts and/or alerts for census periods associated with medical inpatient units that satisfy a defined criterion can be provided. A medical inpatient unit can be, for example, a hospital inpatient unit. In an aspect, emerging census patterns and/or relationships (e.g., complex relationships) associated with medical inpatient units can be predicted. Furthermore, in an embodiment, real-time patient data can be collected from an electronic medical record. The real-time data can be summarized and/or aggregated to provide patient flow information. Additionally or alternatively, historical data can be summarized and/or aggregated to provide patient flow information. Patient flow patterns and/or relationships can be learned via one or more machine learning techniques. In an aspect, percentage of patient inflows and/or patient outflows to and/or from a particular medical inpatient unit can be learning by mining historical patient movements through one or more medical inpatient units (e.g., one or more medical inpatient units that include the particular medical inpatient unit and/or one or more other medical inpatient units). Additionally or alternatively, one or more rules of patient flow can be extracted. The one or more rules can include, for example, a rule such as automatically identify source units, volume and/or medical specialty of patients flowing to a given inpatient unit. In another embodiment, the patient flow in source units can be monitored to detect one or more abnormalities associated with the patient flow. Furthermore, census in inpatient units can be predicted and/or emerging patterns of census in source units can be detected. In yet another embodiment, an alert can be generated to alert a user of one or more census periods that satisfy a defined criterion associated with a defined threshold level.

In certain embodiments, an application programming interface gateway and/or a microservices architecture can be employed to collect and summarize real-time patient data from an electronic medical record. The real-time patient data can, for example, be summarized per workflow process and/or strategy logic for a hospital. Data summarization of the real-time patient data can be carried out in multiple stages. In an example, a first stage can summarize data for individual patients. Furthermore, a second stage can aggregate the real-time patient data at a hospital unit or at a logical entity level. For example, a first stage can summarize when a patient was admitted to a medical inpatient unit and the second stage can summarize the census and total admissions within the hour for the medical inpatient unit. In certain embodiments, an automated learning engine can deduce patient flow patterns and/or can learn patient flow relationships (e.g., complex patient flow relationships) between medical inpatient units and how the patient flow relationships impact inpatient unit census. The automated learning engine can also deduce, for example, hourly census periods or daily census periods associated with one or more medical inpatient units. Using the learning, the automated learning engine can, for example, predict the census for a certain interval of time (e.g., a next 1 hour to 48 hours) and can achieve very high prediction accuracy for one or more inpatient hospital units. The automated learning engine can also employ one or more supervised machine learning methodologies to determine one or more census predictions for one or more inpatient hospital units. In certain embodiments, an alerting engine can generate one or more alerts for periods of census based on configured thresholds. For example, the one or more alerts can be generated once a census prediction is made for an inpatient hospital unit. In certain embodiments, a user interface service can display one or more emerging census patterns, one or more alert notifications, and/or other relevant information on a display device such as, for example, a mobile application for a mobile device, a wall display, a monitor and/or another type of display device.

Compared to a conventional system, the adaptive learning system disclosed herein can provide improved accuracy, reduced time and/or greater adaptability for monitoring, predicting, analyzing and/or alerting associated with real-time patient data for a hospital environment. The adaptive learning system disclosed herein can can also be employed to perform a utility-based analysis associated with real-time patient data for a hospital environment. As such, management of patient data for a hospital environment can be improved. Moreover, performance of systems that monitor real-time patient data for a hospital environment, predict one or more characteristics for real-time patient data for a hospital environment, analyze real-time patient data for a hospital environment, and/or generate an alert associated with real-time patient data for a hospital environment can be improved. Costs associated with the systems can also be reduced.

Referring initially to FIG. 1, there is illustrated an example system 100 that monitors, predicts and/or alerts for census periods associated with medical inpatient units that satisfy a defined criterion, according to an aspect of the subject disclosure. The system 100 can be implemented on or in connection with a network of servers associated with an enterprise application (e.g., an enterprise network of connected machines). The system 100 can be employed by various systems, such as, but not limited to healthcare systems, medical systems, hospital systems, medical device systems, electronic health record systems, electronic medical record systems, forecasting systems, adaptive learning systems, automated learning engine systems, alerting engine systems, machine learning systems, artificial intelligence systems, neural network systems, industrial systems, aviation systems, manufacturing systems, factory systems, energy management systems, power grid systems, water supply systems, transportation systems, refinery systems, media systems, research systems, financial systems, data-driven prognostics systems, network systems, computer network systems, communication systems, router systems, server systems, high availability server systems (e.g., Telecom server systems), Web server systems, file server systems, data server systems, disk array systems, powered insertion board systems, cloud-based systems, and the like. In one example, the system 100 can be associated with a Platform-as-a-Service (PaaS) and/or a medical data management system. Moreover, the system 100 and/or the components of the system 100 can be employed to use hardware and/or software to solve problems that are highly technical in nature (e.g., related to machine learning, related to digital data analysis, related to digital data analytics, etc.), that are not abstract and that cannot be performed as a set of mental acts by a human The system 100 can include a forecasting component 102. In FIG. 1, the forecasting component 102 includes a patient flow component 104, a monitoring engine component 106, a patient census component 108, and an alert component 110. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. The system 100 (e.g., the forecasting component 102) can include memory 114 for storing computer executable components and instructions. The system 100 (e.g., the forecasting component 102) can further include a processor 112 to facilitate operation of the instructions (e.g., computer executable components and instructions) by the system 100 (e.g., the forecasting component 102).

The forecasting component 102 (e.g., the patient flow component 104) can receive patient flow data 116. The patient flow data 116 can be related to a set of patient identities associated with a set of medical inpatient units. Additionally or alternatively, the patient flow data 116 can be related to a set of operations associated with a set of medical inpatient units. The set of medical inpatient units can include one or more medical inpatient units. The set of medical inpatient units can be, for example, a set of hospital inpatient units. For example, a medical inpatient unit from the set of medical inpatient units can be, for example, a hospital unit configured to provide one or more medical services to a group of patients. Furthermore, a medical inpatient unit from the set of medical inpatient units can be associated with a location (e.g., a physical location) within a hospital or a group of hospitals. The patient flow data 116 can include medical data, sensor data, process data (e.g., process log data), monitoring data, maintenance data, parameter data, measurement data, performance data, textual data, audio data, image data, video data, machine data, asset data, equipment data, medical device data, meter data, real-time data, historical data and/or other data. Furthermore, the patient flow data 116 can be encoded data, processed data and/or raw data.

In an embodiment, the patient flow data 116 can include patient data associated with a set of medical inpatient units. The patient data can be, for example, real-time patient data associated with a set of medical inpatient units. The patient data can be associated with one or more patients. In an aspect, the patient data can be generated by one or more devices and/or one or more equipment located within the set of medical inpatient units. For example, the patient data can be generated by one or more medical devices, one or more medical equipment, one or more sensors, one or more mobile devices, one or more computers, one or more tablet computers, and/or one or more other devices. In certain embodiments, the patient data can be generated by one or more surgical instruments such as, but not limited to, one or more anesthetic machines, one or more post anesthetic care machines, surgical tracking software, and/or another type of surgical instrument. Furthermore, the one or more devices and/or one or more equipment located within the set of medical inpatient units can be one or more network-connected devices and/or one or more network-connected equipment. In another aspect, the patient data can be obtained from one or more medical logs. For example, the patient data can be obtained from one or more electronic medical records.

Additionally or alternatively, the patient flow data 116 can include operations data associated with the set of medical inpatient units. The operations data can be associated with one or more operational processes associated with the set of medical inpatient units. For instance, the operations data can include status information associated with one or more medical procedures performed within the set of medical inpatient units, time information associated with one or more medical procedures performed within the set of medical inpatient units, statistical information associated with one or more medical procedures performed within the set of medical inpatient units, efficiency information associated with one or more medical procedures performed within the set of medical inpatient units, and/or other information associated with one or more medical procedures performed within the set of medical inpatient units. The operations data can additionally or alternatively include information associated with medical staff within the set of medical inpatient units. For example, the operations data can include status information associated with medical staff within the set of medical inpatient units, time information associated with medical staff within the set of medical inpatient units, location information associated with medical staff within the set of medical inpatient units, statistical information associated with medical staff within the set of medical inpatient units, efficiency information associated with medical staff within the set of medical inpatient units, and/or other information associated with medical staff within the set of medical inpatient units.

Additionally or alternatively, the patient flow data 116 can include resource data associated with the set of medical inpatient units. The resource data can be associated with one or more resources associated with the set of medical inpatient units. For example, the resource data can include medication information utilized within the set of medical inpatient units, medical supplies information utilized within the set of medical inpatient units, medical equipment information utilized within the set of medical inpatient units, and/or other resource information utilized within the set of medical inpatient units. In another embodiment, the patient flow data 116 can provide aggregated information associated with the patient data, the operations data and/or the resource data. Therefore, the patient flow data 116 can provide information associated with patient flow throughout the set of medical inpatient units. For example, the patient flow data 116 can provide real-time patient flow information throughout the set of medical inpatient units.

The patient flow component 104 can perform a first machine learning process to learn one or more patterns in the patient flow data 116. The patient flow component 104 can perform the first machine learning process to additionally or alternatively learn one or more relationship (e.g., one or more complex relationships) associated with the patient flow data 116. Additionally or alternatively, the first machine learning process performed by the patient flow component 104 can determine one or more rules associated with the patient flow data 116. Additionally or alternatively, the first machine learning process performed by the patient flow component 104 can determine one or more relationships among the set of medical inpatient units. The patient flow component 104 can employ principles of artificial intelligence to facilitate learning one or more patterns in the patient flow data 116, determining one or more rules associated with the patient flow data 116, and/or determining one or more relationships among the set of medical inpatient units. The patient flow component 104 can perform learning associated with the patient flow data 116 explicitly or implicitly. Learning and/or determining inferences by the patient flow component 104 can facilitate identification and/or classification of different patterns associated with the patient flow data 116, determining one or more rules associated with the patient flow data 116, and/or determining one or more relationships among the set of medical inpatient units. The patient flow component 104 can also employ an automatic classification system and/or an automatic classification process to facilitate learning one or more patterns in the patient flow data 116, determining one or more rules associated with the patient flow data 116, and/or determining one or more relationships among the set of medical inpatient units. For example, the patient flow component 104 can employ a probabilistic and/or statistical-based analysis (e.g., factoring into the analysis utilities and costs) to learn one or more patterns in the patient flow data 116, determine one or more rules associated with the patient flow data 116, and/or determine one or more relationships among the set of medical inpatient units. The patient flow component 104 can employ, for example, a support vector machine (SVM) classifier to learn one or more patterns in the patient flow data 116, determine one or more rules associated with the patient flow data 116, and/or determine one or more relationships among the set of medical inpatient units. Additionally or alternatively, the patient flow component 104 can employ other classification techniques associated with Bayesian networks, decision trees and/or probabilistic classification models. Classifiers employed by the patient flow component 104 can be explicitly trained (e.g., via a generic training data) as well as implicitly trained (e.g., via observing user behavior, receiving extrinsic information). For example, with respect to SVM's that are well understood, SVM's are configured via a learning or training phase within a classifier constructor and feature selection module. A classifier is a function that maps an input attribute vector, $x=(x1, x2, x3, x4, xn)$, to a confidence that the input belongs to a class—that is, $f(x)=confidence(class)$.

In an aspect, the patient flow component 104 can include an inference component that can further enhance automated aspects of the patient flow component 104 utilizing in part inference-based schemes to facilitate learning one or more patterns in the patient flow data 116, determining one or more rules associated with the patient flow data 116, and/or determining one or more relationships among the set of medical inpatient units. The patient flow component 104 can employ any suitable machine-learning based techniques, statistical-based techniques and/or probabilistic-based techniques. The patient flow component 104 can additionally or alternatively employ a reduced set of factors (e.g., an optimized set of factors) to facilitate providing a most accurate machine learning model for predicting census in respective medical inpatient units. For example, the patient flow component 104 can employ expert systems, fuzzy logic, SVMs, Hidden Markov Models (HMMs), greedy search algorithms, rule-based systems, Bayesian models (e.g., Bayesian networks), neural networks, other non-linear training techniques, data fusion, utility-based analytical systems, systems employing Bayesian models, etc. In another aspect, the patient flow component 104 can perform a set of machine learning computations associated with the patient flow data 116. For example, the patient flow component 104 can perform a set of clustering machine learning computations, a set of decision tree machine learning computations, a set of instance-based machine learning computations, a set of regression machine learning computations, a set of regularization machine learning computations, a set of rule learning machine learning computations, a set of Bayesian machine learning computations, a set of deep Boltzmann machine computations, a set of deep belief network computations, a set of convolution neural network computations, a set of stacked auto-encoder computations and/or a set of different machine learning computations. The one or more patterns, the one or more rules and/or the one or more relationships determined by the patient flow component 104 can be stored, for example, in a machine learning database and/or the memory 114.

In certain embodiments, the one or more patterns in the patient flow data 116 (e.g., the one or more patterns learned by the first machine learning process) can be configured as one or more digital fingerprints (e.g., one or more digital signatures) that represents one or more digital patterns associated with the patient flow data 116. A digital fingerprint can be a string of bits associated with a portion of the patient flow data 116. A digital fingerprint can also include a set of data values for one or more parameters over a defined period of time associated with the patient flow data 116. In certain implementations, a digital fingerprint can comprise a sequence of sub-fingerprints associated with different patterns in the patient flow data 116. Furthermore, a digital fingerprint can uniquely identify and/or convey a pattern in the patient flow data 116. For example, a digital fingerprint can be a data element that encodes a pattern in the patient flow data 116. A digital fingerprint can also be associated with a timestamp and/or a period of time for the patient flow data 116. The patient flow component 104 can employ one or more digital fingerprinting techniques (e.g., one or more digital fingerprint algorithms) to map at least a portion of the patient flow data 116 into a set of digital fingerprints. For example, the patient flow component 104 can employ a hash technique to generate the set of digital fingerprints associated with the one or more patterns in the patient flow data 116. In another example, the patient flow component 104 can employ a locality sensitive hashing technique to generate the set of digital fingerprints associated with the one or more patterns in the patient flow data 116. In yet example, the patient flow component 104 can employ a random hashing technique to generate the set of digital fingerprints associated with the one or more patterns in the patient flow data 116. In an implementation, a digital fingerprint can comprise min-hash values associated with a portion of the patient flow data 116. For example, a digital fingerprint can comprise a vector of min-hash values associated with a portion of the patient flow data 116. In another example, a digital fingerprint can comprise a band of min-hash values associated with a portion of the patient flow data 116. In yet another example, a digital fingerprint can comprise a locality-sensitive hashing band of min-hash values associated with a portion of the patient flow data 116. However, it is to be appreciated that other types of digital fingerprinting techniques and/or hashing techniques can be employed to generate a digital fingerprint associated with the patient flow data 116.

The monitoring engine component 106 can monitor the one or more patterns in the patient flow data 116. Additionally or alternatively, the monitoring engine component 106 can monitor the one or more rules associated with the patient flow data 116. Additionally or alternatively, the monitoring engine component 106 can monitor the one or more relationships among the set of medical inpatient units. In an aspect, the monitoring engine component 106 can perform a second machine learning process to detect one or more abnormalities associated with the one or more patterns in the patient flow data 116. The one or more abnormalities associated with the one or more patterns in the patient flow data 116 can be one or more anomalies associated with the one or more patterns in the patient flow data 116. For instance, the one or more abnormalities associated with the one or more patterns in the patient flow data 116 can be unique behavior and/or unique characteristics associated with the one or more patterns in the patient flow data 116. In an example, an abnormality associated with the one or more patterns in the patient flow data 116 can be a change or a difference with respect to one or more other predetermined patterns in the patient flow data 116. In certain embodiments, the monitoring engine component 106 can compare the one or more patterns in the patient flow data 116 to one or more other patterns (e.g., one or more predetermined patterns) to facilitate detection of the one or more abnormalities. In an embodiment, the one or more abnormalities associated with the one or more patterns in the patient flow data 116 can predict and/or indicate an event associated with the one or more patterns in the patient flow data 116. A match between a pattern and another pattern can be, for example, approximately an exact match. Alternatively, a match between a pattern and another pattern can be, for example, a fuzzy match. The monitoring engine component 106 can, in certain embodiments, compute similarity between a pattern and another pattern based on one or more pattern recognition techniques, one or more statistical techniques, and/or one or more artificial intelligence techniques. In another embodiment, the monitoring engine component 106 can additionally or alternatively compute similarity between a pattern and another pattern based on a distance metric. For example, the monitoring engine component 106 can compute similarity between a pattern and another pattern based on a Hamming distance. In another example, the monitoring engine component 106 can compute similarity between a pattern and another pattern based on based on a Jaccard distance. However, one or more other mechanisms for computing similarity between a pattern and another pattern can additionally or alternatively be employed.

The monitoring engine component 106 can employ principles of artificial intelligence to facilitate monitoring the one or more patterns in the patient flow data 116 and/or generating the one or more abnormalities associated with the one or more patterns in the patient flow data 116. In certain embodiments, the monitoring engine component 106 can include a prediction component that employs data (e.g., real time data and/or historical data) to monitor a current state of the set of medical inpatient units. Additionally, the monitoring engine component 106 can facilitate prediction of emerging census patterns for the set of medical inpatient units. The monitoring engine component 106 can perform monitoring of one or more patterns in the patient flow data 116 explicitly or implicitly. Learning and/or determining inferences by the monitoring engine component 106 can facilitate monitoring of one or more patterns in the patient flow data 116. The monitoring engine component 106 can also employ an automatic classification system and/or an automatic classification process to facilitate monitoring one or more patterns in the patient flow data 116. For example, the monitoring engine component 106 can employ a probabilistic and/or statistical-based analysis (e.g., factoring into the analysis utilities and costs) to monitor one or more patterns in the patient flow data 116. The monitoring engine component 106 can employ, for example, an SVM classifier to monitor one or more patterns in the patient flow data 116. Additionally or alternatively, the monitoring engine component 106 can employ other classification techniques associated with Bayesian networks, decision trees and/or probabilistic classification models. Classifiers employed by the monitoring engine component 106 can be explicitly trained (e.g., via a generic training data) as well as implicitly trained (e.g., via observing user behavior, receiving extrinsic information). For example, with respect to SVM's that are well understood, SVM's are configured via a learning or training phase within a classifier constructor and feature selection module. A classifier is a function that maps an input attribute vector, $x=(x1, x2, x3, x4, xn)$, to a confidence that the input belongs to a class—that is, $f(x)=\text{confidence}(\text{class})$.

In an aspect, the monitoring engine component 106 can include an inference component that can further enhance automated aspects of the monitoring engine component 106 utilizing in part inference-based schemes to facilitate monitoring of one or more patterns in the patient flow data 116. The monitoring engine component 106 can employ any suitable machine-learning based techniques, statistical-based techniques and/or probabilistic-based techniques. The monitoring engine component 106 can additionally or alternatively employ a reduced set of factors (e.g., an optimized set of factors) to facilitate providing a most accurate machine learning model for predicting census in respective medical inpatient units. For example, the monitoring engine component 106 can employ expert systems, fuzzy logic, SVMs, HMMs, greedy search algorithms, rule-based systems, Bayesian models (e.g., Bayesian networks), neural networks, other non-linear training techniques, data fusion, utility-based analytical systems, systems employing Bayesian models, etc. In another aspect, the monitoring engine component 106 can perform a set of machine learning computations associated with the one or more patterns in the patient flow data 116. For example, the monitoring engine component 106 can perform a set of clustering machine learning computations, a set of decision tree machine learning computations, a set of instance-based machine learning computations, a set of regression machine learning computations, a set of regularization machine learning computations, a set of rule learning machine learning computations, a set of Bayesian machine learning computations, a set of deep Boltzmann machine computations, a set of deep belief network computations, a set of convolution neural network computations, a set of stacked auto-encoder computations and/or a set of different machine learning computations. The one or more abnormalities determined by the monitoring engine component 106 can be stored, for example, in a machine learning database and/or the memory 114.

The patient census component 108 can determine patient census data associated with the patient flow data 116. The patient census data can be associated with a prediction for a total number of patient identities in the set of medical inpatient units during a period of time. For example, patient census data can provide a prediction for a total number of patients that will utilize one or more medical inpatient units from the set of medical inpatient units during a future period of time. The patient census data can additionally or alternatively provide a prediction associated with medical assets in one or more medical inpatient units. For example, the patient census data can predict a total number of beds that will be closed for patient, staffing or maintenance reasons. The patient census data can additionally or alternatively provide one or more predicted emerging patterns in the set of medical inpatient units during the period of time (e.g., the future period of time). The patient census component 108 can determine the patient census data based on the one or more patterns and/or the one or more abnormalities. In certain embodiments, the patient census component 108 can employ data collected in real time to determine the patient census data associated with the patient flow data 116. Additionally or alternatively, the patient census component 108 can employ historical data to determine the patient census data associated with the patient flow data 116. Additionally or alternatively, the patient census component 108 can employ learning and/or prediction to determine the patient census data associated with the patient flow data 116. In an embodiment, the patient census component 108 can determine the patient census data for a given point in time (e.g., a census for a particular medical inpatient unit at 6:00 am, etc.). In another embodiment, the patient census component 108 can determine the patient census data over multiple time periods and/or with different time intervals between predictions.

The alert component 110 can generate alert data 118 based on the patient census data. In an aspect, the alert data 118 generated by the alert component 110 can include one or more alerts for one or more user interfaces. The alert component 110 can generate the alert data 118 (e.g., the alert component 110 can generate the one or more alerts for the one or more user interfaces) in response to a determination that the patient census data satisfies a defined criterion. In an embodiment, the alert component 110 can generate the alert data 118 (e.g., the alert component 110 can generate the one or more alerts for the one or more user interfaces) in response to a determination that the patient census data exceeds a defined threshold. For example, the alert component 110 can generate the alert data 118 (e.g., the alert component 110 can generate the one or more alerts for the one or more user interfaces) in response to a determination that the patient census data indicates an extreme census period for one or more medical inpatient units from the set of medical inpatient units. The alert data 118 can include one or more different alerts that are uniquely configured, displayed and/or generated. In an embodiment, the alert component 110 can provide the alert data 118 (e.g., the alert component 110 can provide the one or more alerts) to a display device such as, for example, a mobile device, a mobile application for a mobile device, a wall display, a monitor and/or another type of display device. In certain embodiments, the alert data 118 (e.g., the one or more alerts) can alter a graphical element and/or a graphical indicator for a user interface. For example, the alert data 118 (e.g., the one or more alerts) can alter a color of a graphical element associated with a user interface. In certain embodiments, the alert component 110 can generate the user interface, for display on the display device, that outputs the alert data 118 and/or the patient census data in a human interpretable format. In certain embodiments, the alert data 118 can provide an indicator associated with one or more emerging census patterns in the set of medical inpatient units. In certain embodiments, the alert component 110 can display real time data in a user-friendly format.

While FIG. 1 depicts separate components in the forecasting component 102, it is to be appreciated that two or more components may be implemented in a common component. Further, it can be appreciated that the design of system 100 and/or the forecasting component 102 can include other component selections, component placements, etc., to facilitate census forecasting for one or more medical inpatient units.

Figure 2:
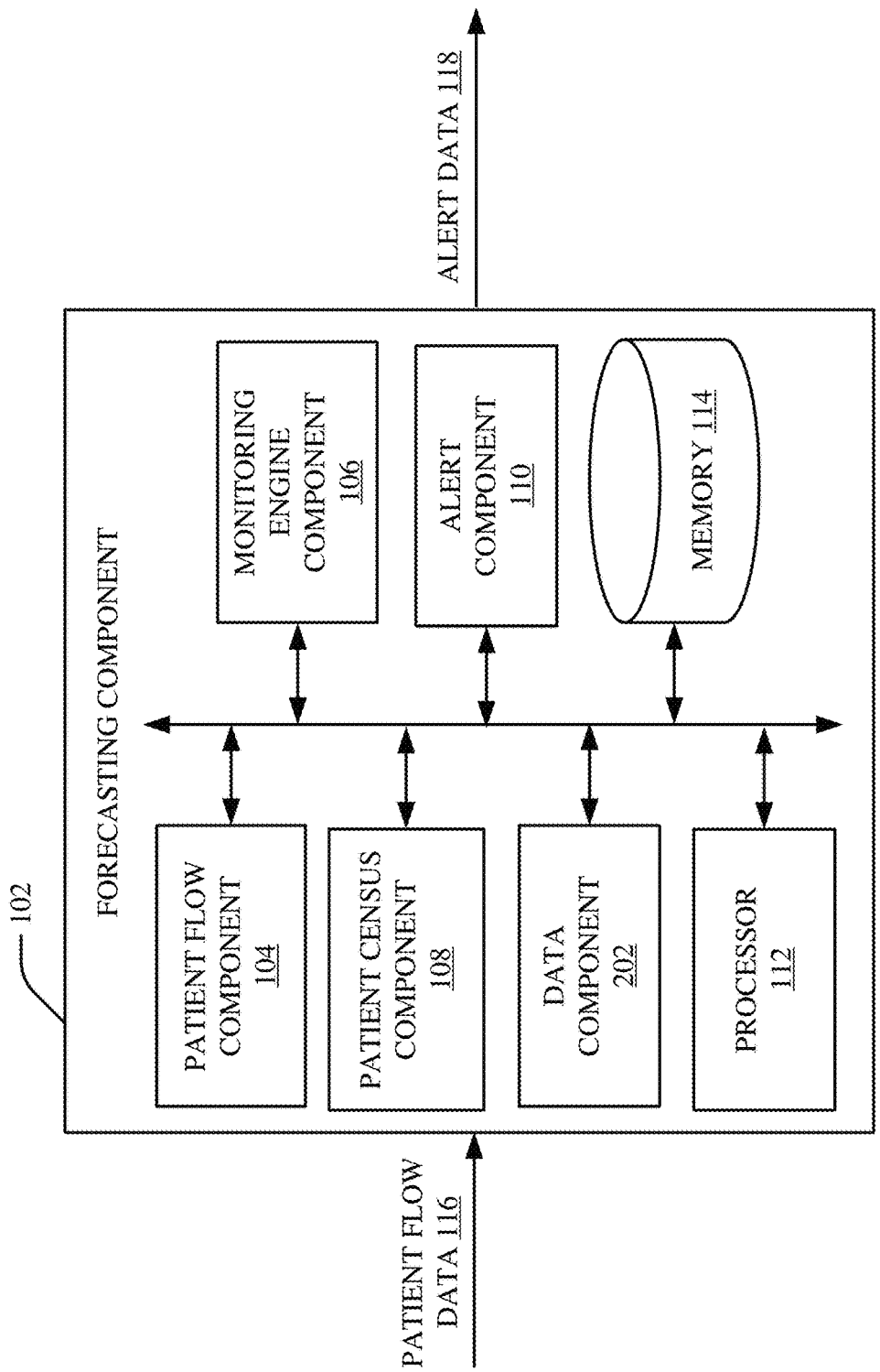
FIG. 2 illustrates a high-level block diagram of another example forecasting component, in accordance with one or more embodiments described herein.

Referring now to FIG. 2, there is illustrated a non-limiting implementation of a system 200 in accordance with various aspects and implementations of this disclosure. Repetitive description of like elements employed in other embodiments described herein is omitted for sake of brevity.

The system 200 includes the forecasting component 102. The forecasting component 102 can include the patient flow component 104, the monitoring engine component 106, the patient census component 108, the alert component 110, a data component 202, the processor 112 and/or the memory 114. The data component 202 can collect at least a portion of the patient flow data 116. For example, the data component 202 can collect the patient data, the operations data and/or the resource data from one or more data sources. In an aspect, the data component 202 can collect at least a portion of the patient flow data 116 from multiple data sources associated with an electronic medical record system. For instance, the data component 202 can collect the patient data, the operations data and/or the resource data from multiple data sources associated with an electronic medical record system. Additionally or alternatively, the data component 202 can collect the patient data, the operations data and/or the resource data from multiple devices and/or multiple equipment located within the set of medical inpatient units. In an embodiment the data component 202 can aggregate the patient data, the operations data and/or the resource data to generate the patient flow data 116. Additionally or alternatively, the data component 202 can summarize the patient data, the operations data and/or the resource data based on data associated with a set of patient identities. For example, the data component 202 can group the patient data, the operations data and/or the resource data based on a corresponding patient identity (e.g., a corresponding patient). Additionally or alternatively, the data component 202 can summarize the patient data, the operations data and/or the resource data based on data associated with the set of medical inpatient units. For example, the data component 202 can group the patient data, the operations data and/or the resource data based on a corresponding medical inpatient unit. In an embodiment, the data component 202 can transform the patient data, the operations data and/or the resource data into a data format associated with machine learning. Additionally or alternatively, the data component 202 can transform the patient flow data 116 into a data format associated with machine learning.

While FIG. 2 depicts separate components in the forecasting component 102, it is to be appreciated that two or more components may be implemented in a common component. Further, it can be appreciated that the design of system 200 and/or the forecasting component 102 can include other component selections, component placements, etc., to facilitate census forecasting for one or more medical inpatient units.

Figure 3:
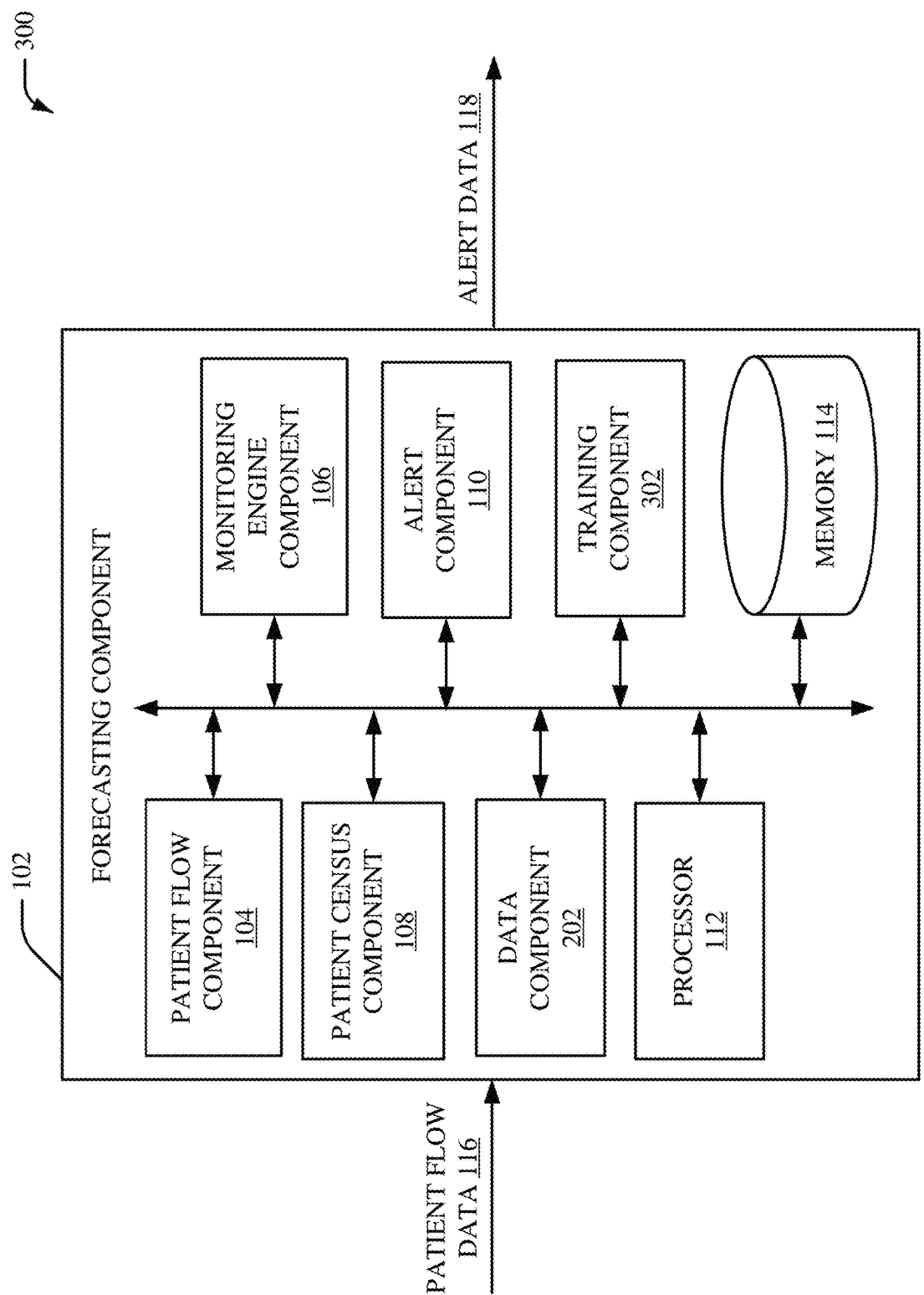
FIG. 3 illustrates a high-level block diagram of yet another example forecasting component, in accordance with one or more embodiments described herein.

Referring now to FIG. 3, there is illustrated a non-limiting implementation of a system 300 in accordance with various aspects and implementations of this disclosure. Repetitive description of like elements employed in other embodiments described herein is omitted for sake of brevity.

The system 300 includes the forecasting component 102. The forecasting component 102 can include the patient flow component 104, the monitoring engine component 106, the patient census component 108, the alert component 110, the data component 202, a training component 302, the processor 112 and/or the memory 114. The training component 302 can generate one or more machine learning models. A machine learning model can extract dominant factors for a given medical inpatient unit. A machine learning model can additionally or alternately extract time series information such as trends, seasonality trends, intervals and/or cycles that affect census in a given medical inpatient unit. A machine learning model can additionally or alternately estimate duration of patients to move from a given medical inpatient unit to another medical inpatient unit. In an embodiment, the training component 302 can generate a first machine learning model for the first machine learning process associated with learning the one or more patterns in the patient flow data 116. The training component 302 can generate the first machine learning model for the first machine learning process based on the patient flow data 116. For example, the training component 302 can generate the first machine learning model for the first machine learning process based on the patient data, the operations data and/or the resource data. Additionally or alternatively, the training component 302 can generate a second machine learning model for the second machine learning process associated with detecting the one or more abnormalities with respect to the one or more patterns in the patient flow data 116. The training component 302 can generate the second machine learning model for the second machine learning process based on the patient flow data 116. For example, the training component 302 can generate the second machine learning model for the second machine learning process based on the patient data, the operations data and/or the resource data. In an embodiment, the training component 302 can tune one or more parameters for a machine learning model based on an evaluation of the patient census data. For example, the training component 302 can tune one or more parameters for the first machine learning model associated with the first machine learning process based on an evaluation of the patient census data. Additionally or alternatively, the training component 302 can tune one or more parameters for the second machine learning model associated with the second machine learning process based on an evaluation of the patient census data. In an embodiment, the training component 302 can learn one or more patters associated with the patient flow data 116. The training component 302 can also estimate patient flow relationships (e.g., complex patient flow relationships) associated with the patient flow data 116. The training component 302 can employ the estimated patient flow relationships to tune tunes one or more parameters for a machine learning model.

While FIG. 3 depicts separate components in the forecasting component 102, it is to be appreciated that two or more components may be implemented in a common component. Further, it can be appreciated that the design of system 300 and/or the forecasting component 102 can include other component selections, component placements, etc., to facilitate census forecasting for one or more medical inpatient units.

Figure 4:
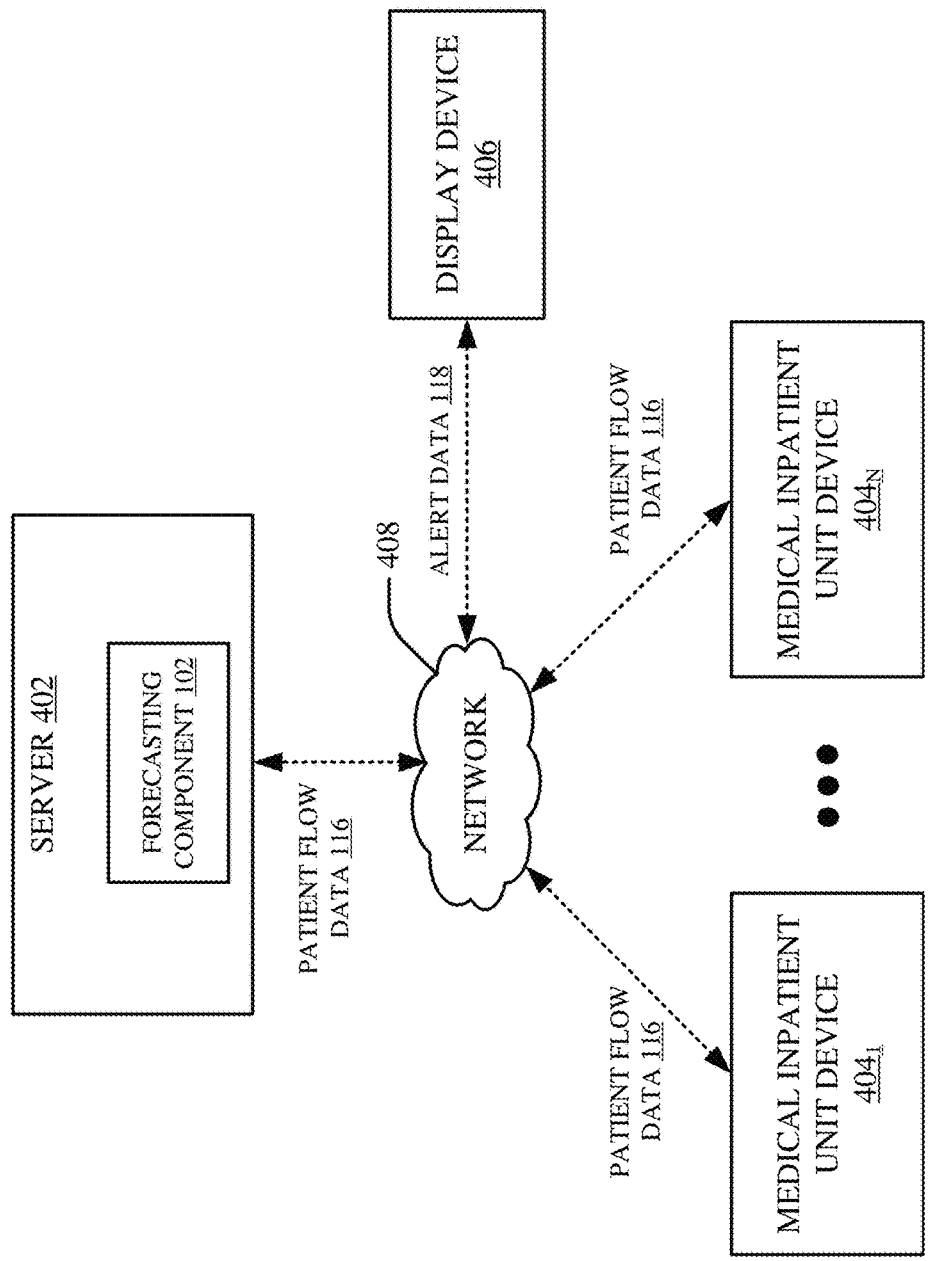
FIG. 4 illustrates an example system for monitoring, predicting and/or alerting for census periods in medical inpatient units, in accordance with one or more embodiments described herein.

Referring to FIG. 4, there is illustrated a non-limiting implementation of a system 400 in accordance with various aspects and implementations of this disclosure. Repetitive description of like elements employed in other embodiments described herein is omitted for sake of brevity.

The system 400 includes a server 402, a set of medical inpatient unit devices $404_{1-N}$, and a display device 406, where N is an integer. The server 402 can include the forecasting component 102. Furthermore, the set of medical inpatient unit devices $404_{1-N}$ can be associated with a set of medical inpatient units. For example, the set of medical inpatient unit devices $404_{1-N}$ can be included in one or more medical inpatient units. In a non-limiting example, a medical inpatient unit device $404_1$ can be located in a first medical inpatient unit, a medical inpatient unit device $404_2$ can be located in a second medical inpatient unit, and a medical inpatient unit device $404_N$ can be located in an Nth medical inpatient unit. The set of medical inpatient unit devices $404_{1-N}$ can be one or more devices and/or one or more equipment located within the set of medical inpatient units. For example, set of medical inpatient unit devices $404_{1-N}$ can be one or more medical devices, one or more medical equipment, one or more sensors, one or more mobile devices, one or more computers, one or more tablet computers, and/or one or more other devices. Furthermore, the set of medical inpatient unit devices $404_{1-N}$ can be can be one or more network-connected devices communicatively coupled to the server 402. The server 402, the set of medical inpatient unit devices $404_{1-N}$, and/or the display device 406 can be in communication via a network 408. The network 408 can be a communication network, a wireless network, an internet protocol (IP) network, a voice over IP network, an internet telephony network, a mobile telecommunications network and/or another type of network. The display device 406 can be a mobile device, a mobile application for a mobile device, a wall display, a monitor, a computer, a tablet computer, a wearable device, and/or another type of display device. In an embodiment, the set of medical inpatient unit devices $404_{1-N}$ can provide the patient flow data 116 to the forecasting component 102 of the server 402 via the network 408. Additionally or alternatively, the forecasting component 102 of the server 402 can provide the alert data 118 to the display device 406 via the network 408.

In an embodiment, the system 400 can be a microservices architecture that can collect and/or aggregate the patient flow data 116 from one or more hospital systems associated with the set of medical inpatient unit devices $404_{1-N}$. The forecasting component 102 can employ one or more machine learning techniques to learn patient flow patterns, deduce rules and establish complex relationships between the set of medical inpatient unit devices $404_{1-N}$ using the patient flow data 116. The forecasting component 102 can also employ one or more machine learning techniques to monitor patient flow patterns and detect abnormalities in patient flow associated with the patient flow data 116. Furthermore, the forecasting component 102 can employ one or more machine learning techniques to predict census at one or more medical inpatient units associated with the set of medical inpatient unit devices $404_{1-N}$. The display device 406 can be employed to alert users (e.g., administrators, medical staff, doctors, nurses, etc.) of emerging census patterns associated with the patient flow data 116 and/or the set of medical inpatient unit devices $404_{1-N}$.

In another embodiment, the system 400 can be an adaptive machine learning system that employs patient data, operations data and/or resource data associated with the patient flow data 116. The forecasting component 102 can learn one or more aspects of hospital operations associated with the set of medical inpatient unit devices 404$_{1-N}$, automatically adapt to policy changes of a hospital (e.g. a new policy can state that half of the patients in a medical inpatient unit can be surgical patients because of nurse credentials), and/or detect emerging patterns of census in the medical inpatient units over a future time horizon (e.g., up to 48 hours) with improved accuracy. As such, the system 400 can analytics in combination with hospital knowledge to obtain an accurate, holistic view throughout an entire health system. Accordingly, better care for patients can be provided, improved access for patients can be provided, costs for a medical system can be reduced, and/or revenue opportunities for a hospital can be increased.

In yet another embodiment, the system 400 can provide one or more microservices that can be tailored and/or configured to the collect a specific type of data at a desired frequency. For example, a portion of the patient flow data 116 can be pushed and/or collected in real time while another portion of the patient flow data 116 can be batched and/or pulled periodically. The forecasting component 102 can facilitate communication of microservices across service boundaries. The forecasting component 102 can also integrate and/or aggregate the patient flow data 116 for artificial intelligence-based analytics. The forecasting component 102 can provide a machine learning engine combined with heuristic algorithms to combine results of multiple machine learning models. Additionally or alternatively, the forecasting component 102 can provide spectral analysis to detect patient flow patterns associated with one or more medical inpatient units. Patient flow patterns can observe a volume of patients moving between medical inpatient units by hour, time of day, day of week, medical specialty, current occupancy levels, business rules and/or one or more other factors. The machine learning engine of the forecasting component 102 can also extract one or more rules and/or can create one or more machine learning models for the patient flow patterns.

The forecasting component 102 can also monitors the patient flow patterns associated with the patient flow data 116 and can detect one or more changes to the flow patterns beyond pre-determined thresholds. The forecasting component 102 can also predict medical inpatient unit census based on flow patterns and cam provide one or more alerts to the display device 406 if the emerging patterns of census are beyond configured limits. In certain embodiments, the limits can be learned from normal operating patterns of a hospital system to assist in setting the thresholds. An alert engine of the forecasting component 102 can create and/or display one or more alerts regarding the emerging census patterns using one or more user interface services associated with the display device 406.

Figure 5:
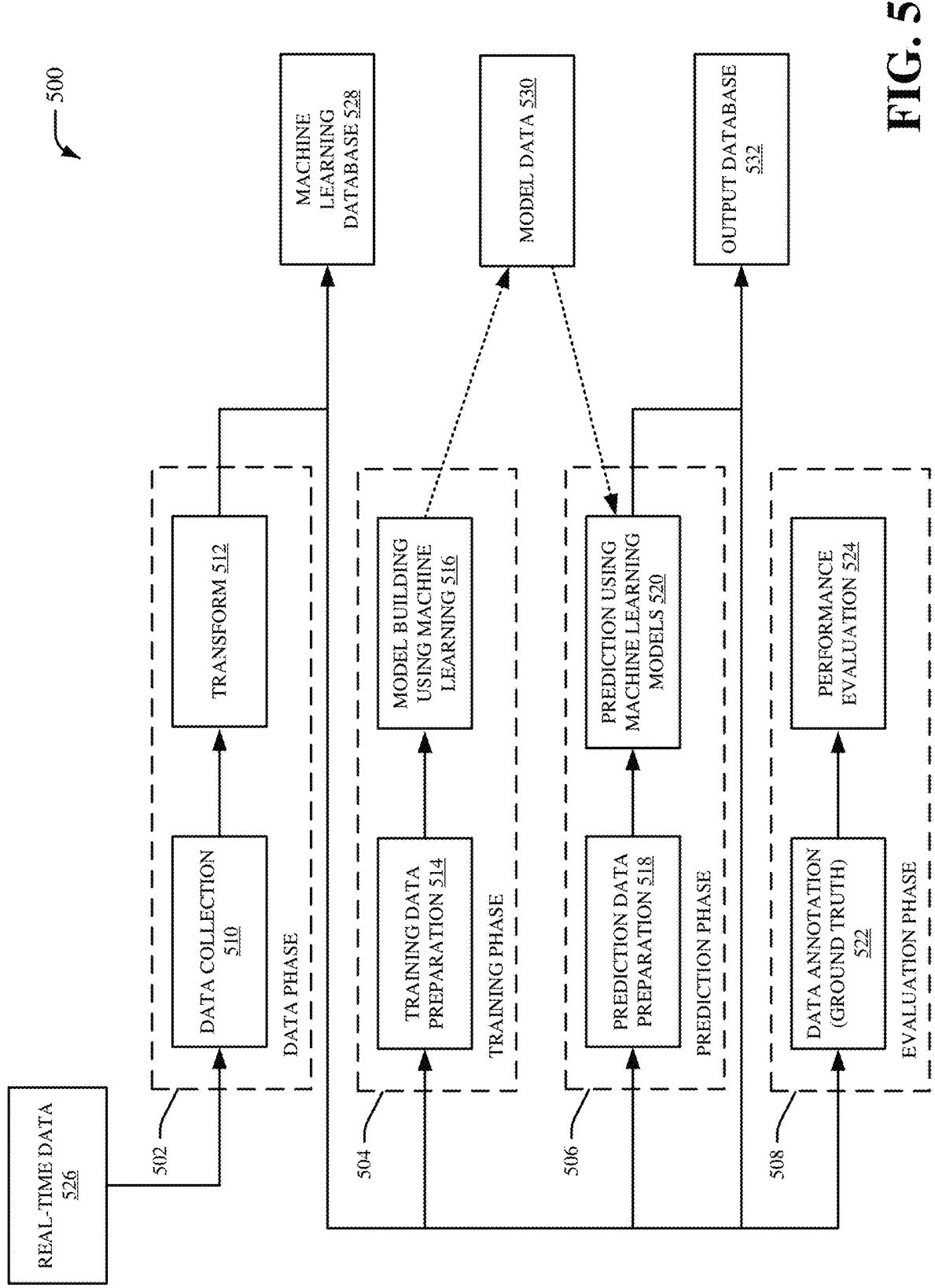
FIG. 5 illustrates an example system associated with a machine learning process for monitoring, predicting and/or alerting for census periods in medical inpatient units, in accordance with one or more embodiments described herein.

Referring to FIG. 5, there is illustrated a non-limiting implementation of a system 500 in accordance with various aspects and implementations of this disclosure. Repetitive description of like elements employed in other embodiments described herein is omitted for sake of brevity.

The system 500 includes a data phase 502, a training phase 504, a prediction phase 506 and/or an evaluation phase 508. The data phase 502, the training phase 504, the prediction phase 506 and/or the evaluation phase 508 can be executed during a machine learning process. For example, the data phase 502, the training phase 504, the prediction phase 506 and/or the evaluation phase 508 can be respective phases of a machine learning process. The data phase 502 can include a step 510 associated with data collection. The data phase 502 can additionally or alternatively include a step 512 associated with a transform. The training phase 504 can include a step 514 associated with training data preparation. The training phase 504 can additionally or alternatively include a step 516 associated with model building using machine learning. The prediction phase 506 can include a step 518 associated with prediction data preparation. The prediction phase 506 can additionally or alternatively include a step 520 associated with prediction using machine learning models. The evaluation phase 508 can include a step 522 associated data annotation (ground truth). The evaluation phase 508 can additionally or alternatively include a step 524 associated with performance evaluation.

In an embodiment, real-time data 526 can be provided to the data phase 502. For instance, the step 510 of the data phase 502 can perform data collection to collect the real-time data 526. The real-time data 526 can be associated with patient flow data. For example, the real-time data 526 can be related to a set of patient identities associated with a set of medical inpatient units. Additionally or alternatively, the real-time data 526 can be related to a set of operations associated with a set of medical inpatient units. In certain embodiments, the real-time data 526 can correspond to the patient flow data 116. The real-time data 526 can include medical data, sensor data, process data (e.g., process log data), monitoring data, maintenance data, parameter data, measurement data, performance data, textual data, audio data, image data, video data, machine data, asset data, equipment data, medical device data, meter data, real-time data, historical data and/or other data. Furthermore, the real-time data 526 can be encoded data, processed data and/or raw data. In certain embodiments, the real-time data 526 can include the patient data associated with a set of medical inpatient units. Additionally or alternatively, the real-time data 526 can include the operations data associated with the set of medical inpatient units. Additionally or alternatively, the real-time data 526 can include resource data associated with the set of medical inpatient units. The step 512 of the data phase 502 can transform the real-time data 526 into data for use by the training phase 504 of the machine learning process, the prediction phase 506 of the machine learning process, and/or the evaluation phase 508 of the machine learning process. In another embodiment, the data generated by the step 512 (e.g., the transformed real-time data) can be stored in a machine learning database 528.

In another embodiment, the step 514 of the training phase 504 can employ the data stored in the machine learning database 528 to prepare training data for machine learning. The step 516 of the training phase 504 can employ the training data to build a model using machine learning. For example, the step 516 of the training phase 504 can employ the training data to build a machine learning model. Model data 530 can, for example, correspond to the machine learning model generated at step 516. The model data 530 (e.g., the machine learning model) can be associated with one or more patterns in the real-time data 526 related to a set of patient identities and a set of operations associated with a set of medical inpatient units. Additionally or alternatively, the model data 530 (e.g., the machine learning model) can be associated with one or more abnormalities associated with the one or more patterns in the real-time data 526. In yet another embodiment, the step 518 of the prediction phase 506 can employ the data stored in the machine learning database 528 to prepare prediction data for machine learning. The step 520 of the prediction phase 506 can employ the prediction data to predict using machine learning models. For example, the step 520 of the prediction phase 506 can employ the prediction data from step 518 and/or the model data 530 to predict patient census data associated with a prediction for a total number of patient identities in the set of medical inpatient units during a period of time. The prediction determined by the step 520 can be stored in an output database 532. In yet another embodiment, the step 522 of the evaluation phase 508 can employ the data stored in the machine learning database 528 for data annotation. For example, the step 522 of the evaluation phase 508 can employ the data stored in the machine learning database 528 to determine ground truth accuracy of the prediction generated by the step 520. The step 524 of the evaluation phase 508 can evaluate performance of the machine learning process based on the data annotation from the step 522. For example, the step 524 of the evaluation phase 508 can employ one or more metrics to determine classification accuracy of the prediction determined by the step 520 of the prediction phase 506.

Figure 6:
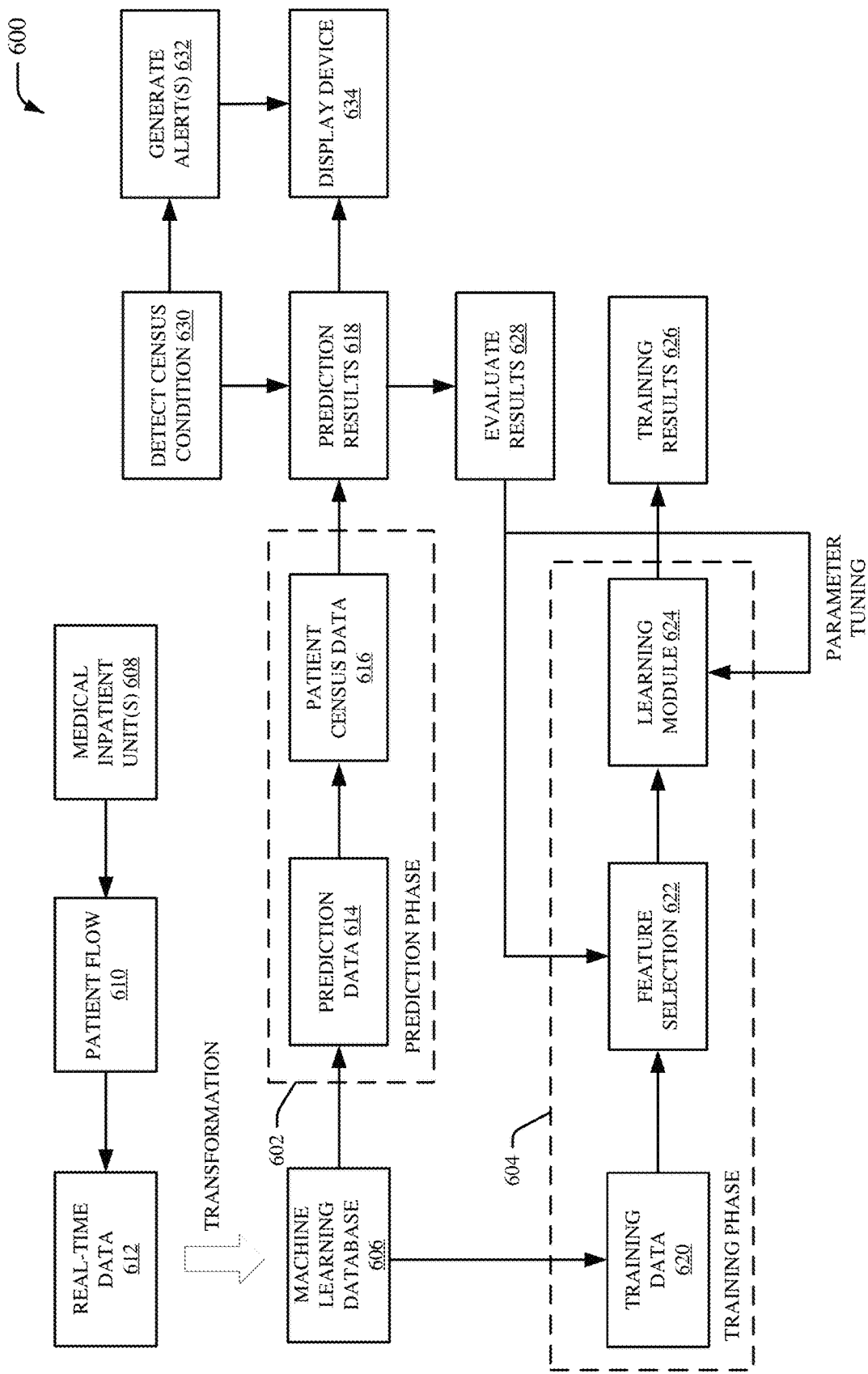
FIG. 6 illustrates an example system associated with another machine learning process for monitoring, predicting and/or alerting for census periods in medical inpatient units, in accordance with one or more embodiments described herein.

Referring to FIG. 6, there is illustrated a non-limiting implementation of a system 600 in accordance with various aspects and implementations of this disclosure. Repetitive description of like elements employed in other embodiments described herein is omitted for sake of brevity.

The system 600 includes a prediction phase 602 and a training phase 604 for a machine learning process. The prediction phase 602 and/or the training phase 604 can employ data from a machine learning database 606. The machine learning database 606 can employ data from one or more medical inpatient units 608 to determine patient flow 610 and to generate real-time data 612. The real-time data 612 can undergo a transformation into the data stored in the machine learning database 606 for machine learning. Based on the data stored in the machine learning database 606, the prediction phase 602 can generate prediction data 614. The prediction phase 602 can also employ the prediction data 614 to generate patient census data 616. The patient census data 616 can provide a prediction for patient census in the one or more medical inpatient units 608 during a period of time (e.g., a future period of time). The patient census data 616 can be provided a prediction results 618 for the one or more medical inpatient units 608. Additionally or alternatively, based on the data stored in the machine learning database 606, the training phase 604 can generate training data 620. Feature selection 622 of the training phase 604 can employ the training data 620 for selecting one or more features to generate a machine learning model. A learning module 624 of the training phase 604 can be employed to build one or more machine learning models based on the feature selection 622. Training results 626 of the training phase 604 can be generated by the learning module 624. In an embodiment, evaluate results 628 can be employed to evaluate the prediction results 618. The evaluate results 628 can be employed by the feature selection 622 of the training phase 604. Additionally or alternatively, evaluate results 628 can be employed for parameter tuning associated with the learning module 624. For example, the evaluate results 628 can be employed to tune one or more parameters of a machine learning module generated by the learning module 624. In another embodiment, detect census condition 630 can be employed to detect a condition associated with the patient census data 616. For instance, the detect census condition 630 can be employed to detect whether the patient census data 616 satisfies a defined criterion associated with a defined threshold level (e.g., the detect census condition 630 can be employed to detect an extreme census condition). Based on the detected census condition, generate alert(s) 632 can generate one or more alerts for a user interface. For example, one or more alerts can be generated for a user interface in response to a determination that the patient census data 616 satisfies the defined criterion. Furthermore, the one or more alerts can be presented on a display device 634.

Figure 7:
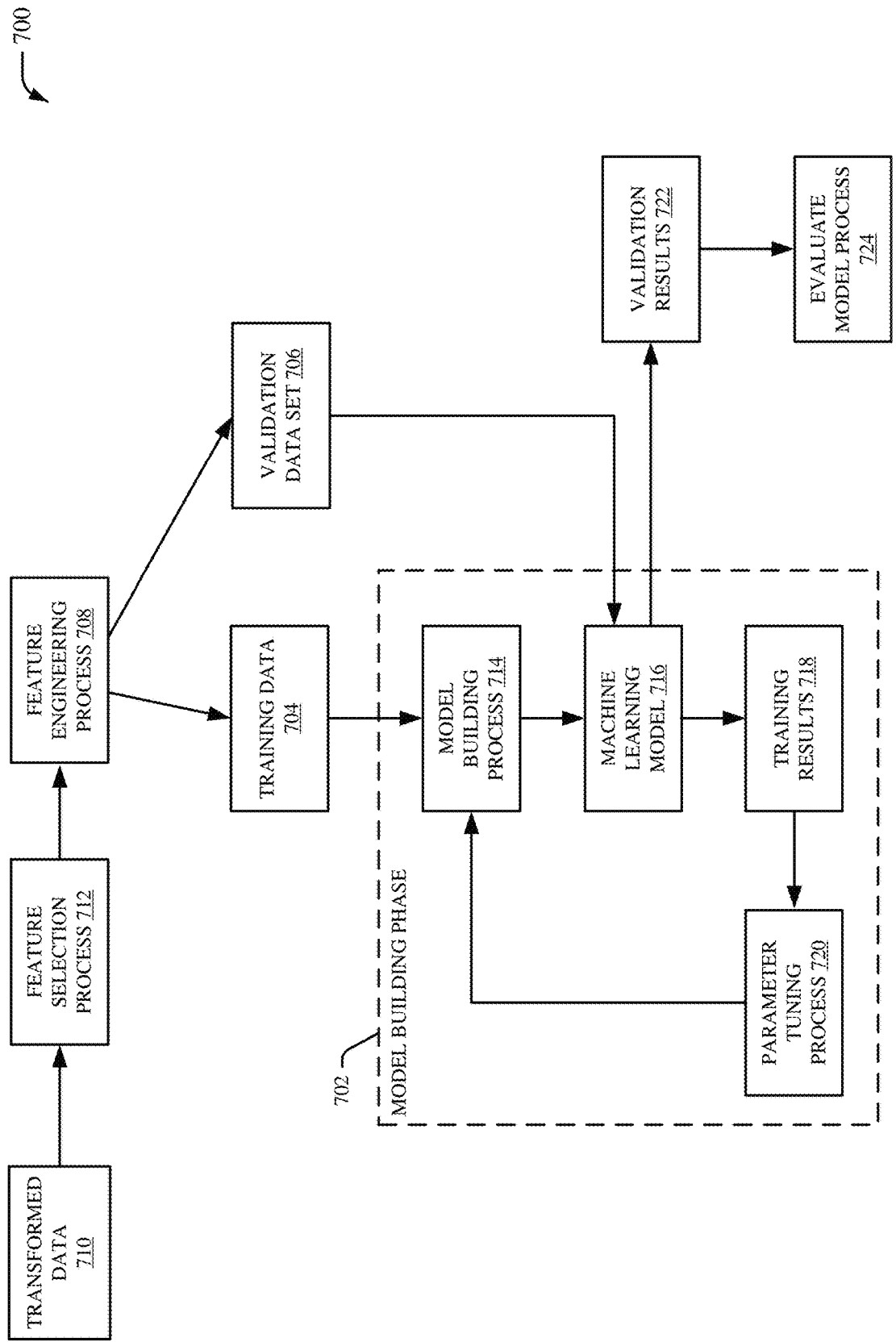
FIG. 7 illustrates an example system associated with yet another machine learning process for monitoring, predicting and/or alerting for census periods in medical inpatient units, in accordance with one or more embodiments described herein.

Referring to FIG. 7, there is illustrated a non-limiting implementation of a system 700 in accordance with various aspects and implementations of this disclosure. Repetitive description of like elements employed in other embodiments described herein is omitted for sake of brevity.

The system 700 includes a model building phase 702 for a machine learning process. The model building phase 702 can employ training data 704 and/or validation data set 706. In an embodiment, training data 704 and/or validation data set 706 can be generated via a feature engineering process 708. The feature engineering process 708 can employ a machine learning process to generate the training data 704 and/or validation data set 706. For example, the feature engineering process 708 can employ a training phase of a machine learning process to generate the training data 704. Additionally or alternatively, the feature engineering process 708 can employ a prediction phase of a machine learning process to generate the validation data set 706. In certain embodiments, transformed data 710 (e.g., transformed data 710 stored in a machine learning database) can be employed by a feature selection process 712. The transformed data 710 can be, for example, a transformed version of real-time data and/or a transformed version of patient flow data. The feature selection process 712 can select one or more features to build one or more machine learning models via the feature engineering process 708. In another embodiment, the model building phase 702 can include a model building process 714. The model building process 714 can build one or more machine learning models associated with the transformed data 710. For example, the model building process 714 can build a machine learning model 716 based on the training data 704 and/or the validation data set 706. The machine learning model 716 can be associated with one or more patterns in the transformed data 710 related to a set of patient identities and a set of operations associated with a set of medical inpatient units. Additionally or alternatively, the machine learning model 716 can be associated with one or more abnormalities associated with the one or more patterns in the transformed data 710. In an aspect, the machine learning model 716 can provide training results 718. Furthermore, a parameter tuning process 720 can be performed based on the training results 718 to tune one or more parameters for the model building process 714. In another aspect, the machine learning model 716 can provide validation results 722 to validate the machine learning model 716. The validation results 722 can be employed by an evaluate model process 724 to evaluate one or more metrics for the machine learning model 716.

Figure 8:
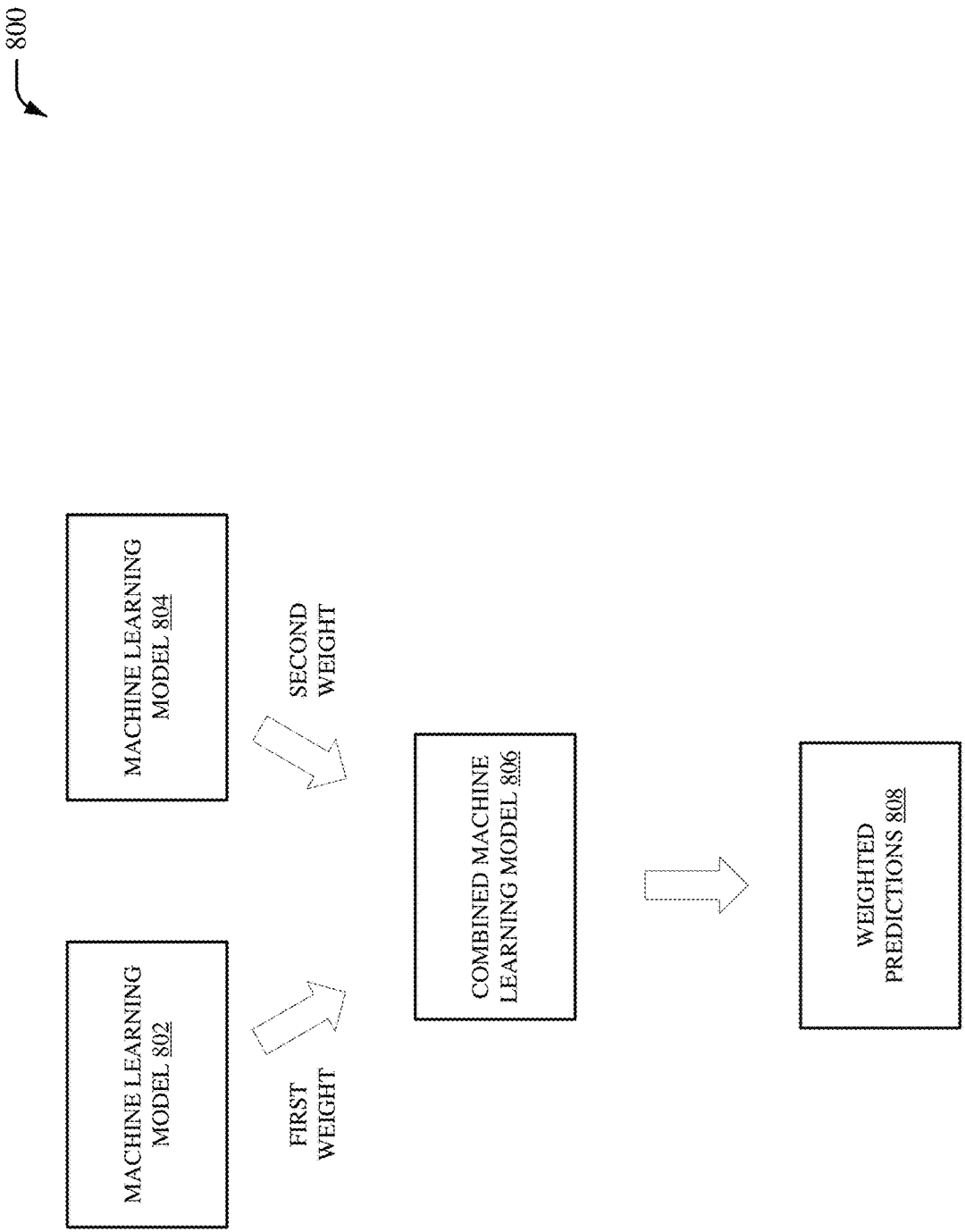
FIG. 8 illustrates an example system associated with combining machine learning models, in accordance with one or more embodiments described herein.

Referring to FIG. 8, there is illustrated a non-limiting implementation of a system 800 in accordance with various aspects and implementations of this disclosure. Repetitive description of like elements employed in other embodiments described herein is omitted for sake of brevity.

The system 800 includes a machine learning model 802 and a machine learning model 804. In an embodiment, the machine learning model 802 and the machine learning model 804 can be corresponding machine learning models. In an alternate embodiment, the machine learning model 802 and the machine learning model 804 can be different machine learning models. The machine learning model 802 and the machine learning model 804 can be employed, for example, to predict patient census data associated with a prediction for a total number of patient identities in the set of medical inpatient units during a period of time based on one or more patterns and/or one or more abnormalities associated with patient flow data. In another embodiment, the machine learning model 802 and/or the machine learning model 804 can include a plurality of forecast models for different period of time to predict patient census data associated with a prediction for a total number of patient identities in the set of medical inpatient units. For example, the machine learning model 802 can include a first forecast model for patient census data associated with a first period of time (e.g., a first forecast model for hour 1), a second forecast model for patient census data associated with a second period of time (e.g., a second forecast model for hour 2), a third forecast model for patient census data associated with a third period of time (e.g., a third forecast model for hour 3), a fourth forecast model for patient census data associated with a fourth period of time (e.g., a fourth forecast model for hour 4), a fifth forecast model for patient census data associated with a fifth period of time (e.g., a fifth forecast model for hours 5-8), a sixth forecast model for patient census data associated with a sixth period of time (e.g., a sixth forecast model for hours 9-12), a seventh forecast model for patient census data associated with a seventh period of time (e.g., a seventh forecast model for hours 12-24), and/or an eight forecast model for patient census data associated with an eighth period of time (e.g., an eighth forecast model for hours 25-48). Additionally, the machine learning model 804 can include a first forecast model for patient census data associated with a first period of time (e.g., a first forecast model for hour 1), a second forecast model for patient census data associated with a second period of time (e.g., a second forecast model for hour 2), a third forecast model for patient census data associated with a third period of time (e.g., a third forecast model for hour 3), a fourth forecast model for patient census data associated with a fourth period of time (e.g., a fourth forecast model for hour 4), a fifth forecast model for patient census data associated with a fifth period of time (e.g., a fifth forecast model for hours 5-8), a sixth forecast model for patient census data associated with a sixth period of time (e.g., a sixth forecast model for hours 9-12), a seventh forecast model for patient census data associated with a seventh period of time (e.g., a seventh forecast model for hours 12-24), and/or an eight forecast model for patient census data associated with an eighth period of time (e.g., an eighth forecast model for hours 25-48).

In an embodiment, different weights can be applied to the machine learning model 802 and the machine learning model 804 to generate a combined machine learning model 806. For instance, a first weight can be applied to the machine learning model 802 and a second weight can be applied to the machine learning model 804. Furthermore, the machine learning model 802 associated with the first weight can be combined with the machine learning model 804 associated with the second weight to generate the combined machine learning model 806. In an aspect, the machine learning model 802 can be a first machine learning model associated with a first weight and the machine learning model 804 can be a second machine learning model associated with a second weight that is different than the first weight. In a non-limiting example, the machine learning model 802 can be associated with a 60% weight and the machine learning model 804 can be associated with a 40% weight. However, it is to be appreciated that different weights can be applied to the machine learning model 802 and/or the machine learning model 804. The combined machine learning model 806 can provide one or more weighted predictions 808. For instance, the one or more weighted predictions 808 can be one or more weighted predictions for the patient census data associated with a prediction for a total number of patient identities in the set of medical inpatient units during one or more different periods of time. In an example, the combined machine learning model 806 can provide a weighted first forecast model for patient census data associated with a first period of time (e.g., a first forecast model for hour 1), a weighted second forecast model for patient census data associated with a second period of time (e.g., a second forecast model for hour 2), a weighted third forecast model for patient census data associated with a third period of time (e.g., a third forecast model for hour 3), a weighted fourth forecast model for patient census data associated with a fourth period of time (e.g., a fourth forecast model for hour 4), a weighted fifth forecast model for patient census data associated with a fifth period of time (e.g., a fifth forecast model for hours 5-8), a weighted sixth forecast model for patient census data associated with a sixth period of time (e.g., a sixth forecast model for hours 9-12), a weighted seventh forecast model for patient census data associated with a seventh period of time (e.g., a seventh forecast model for hours 12-24), and/or a weighted eight forecast model for patient census data associated with an eighth period of time (e.g., an eighth forecast model for hours 25-48). In an aspect, the combined machine learning model 806 and/or the one or more weighted predictions 808 can provide improved accuracy for predicting patient census data.

The aforementioned systems and/or devices have been described with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components may be combined into a single component providing aggregate functionality. The components may also interact with one or more other components not specifically described herein for the sake of brevity, but known by those of skill in the art.

Figure 9:
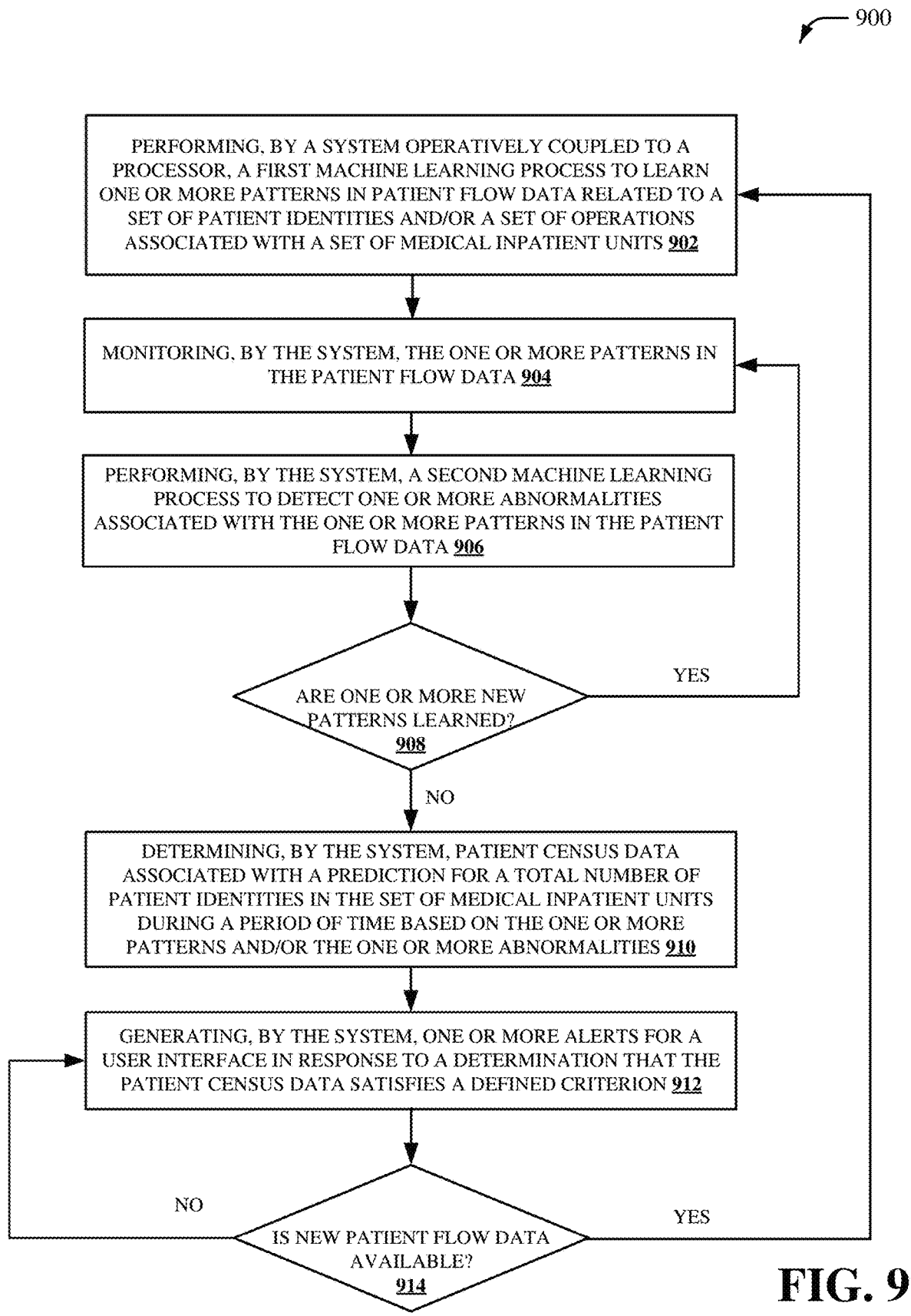
FIG. 9 depicts a flow diagram of an example method for monitoring, predicting and/or alerting for census periods in medical inpatient units, in accordance with one or more embodiments described herein.

FIG. 9 illustrates one or more methodologies and/or flow diagrams in accordance with the disclosed subject matter. For simplicity of explanation, the one or more methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the one or more methodologies in accordance with the disclosed subject matter. In addition, those skilled in the art will understand and appreciate that the one or more methodologies could alternatively be represented as a series of interrelated states via a state diagram or events. Additionally, it should be further appreciated that the one or more methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device or storage media.

Referring to FIG. 9, there illustrated is a methodology 900 for monitoring, predicting and/or alerting for census periods in medical inpatient units, in accordance with one or more embodiments described herein. Repetitive description of like elements employed in other embodiments described herein is omitted for sake of brevity.

As an example, the methodology 900 can be utilized in various applications, such as, but not limited to, healthcare systems, medical systems, hospital systems, medical device systems, electronic health record systems, electronic medical record systems, forecasting systems, adaptive learning systems, automated learning engine systems, alerting engine systems, machine learning systems, artificial intelligence systems, neural network systems, industrial systems, aviation systems, manufacturing systems, factory systems, energy management systems, power grid systems, water supply systems, transportation systems, refinery systems, media systems, research systems, financial systems, data-driven prognostics systems, network systems, computer network systems, communication systems, router systems, server systems, high availability server systems (e.g., Telecom server systems), Web server systems, file server systems, data server systems, disk array systems, powered insertion board systems, cloud-based systems, and the like. In one example, the system 100 can be associated with a PaaS and/or a medical data management system, etc. At 902, a first machine learning process is performed, by a system operatively coupled to a processor (e.g., by patient flow component 104), to learn one or more patterns in patient flow data related to a set of patient identities and/or a set of operations associated with a set of medical inpatient units. Additionally or alternatively, the first machine learning process can determine one or more rules associated with the patient flow data. Additionally or alternatively, the first machine learning process can determine one or more relationships among the set of medical inpatient units. In an embodiment, principles of artificial intelligence can be employed to facilitate learning one or more patterns in the patient flow data, determining one or more rules associated with the patient flow data, and/or determining one or more relationships among the set of medical inpatient units. For example, one or more machine learning techniques can be employed to facilitate learning one or more patterns in the patient flow data, determining one or more rules associated with the patient flow data, and/or determining one or more relationships among the set of medical inpatient units. The set of medical inpatient units can include one or more medical inpatient units. A medical inpatient unit from the set of medical inpatient units can be, for example, a hospital unit configured to provide one or more medical services to a group of patients. Furthermore, a medical inpatient unit from the set of medical inpatient units can be associated with a location (e.g., a physical location) within a hospital or a group of hospitals. The patient flow data can include medical data, sensor data, process data (e.g., process log data), monitoring data, maintenance data, parameter data, measurement data, performance data, textual data, audio data, image data, video data, machine data, asset data, equipment data, medical device data, meter data, real-time data, historical data and/or other data. Furthermore, the patient flow data can be encoded data, processed data and/or raw data.

In certain embodiments, the patient flow data can include patient data associated with a set of medical inpatient units. The patient data can be, for example, real-time patient data associated with a set of medical inpatient units. The patient data can be associated with one or more patients. In an aspect, the patient data can be generated by one or more devices and/or one or more equipment located within the set of medical inpatient units. For example, the patient data can be generated by one or more medical devices, one or more medical equipment, one or more sensors, one or more mobile devices, one or more computers, one or more tablet computers, and/or one or more other devices. Furthermore, the one or more devices and/or one or more equipment located within the set of medical inpatient units can be one or more network-connected devices and/or one or more network-connected equipment. In another aspect, the patient data can be obtained from one or more medical logs. For example, the patient data can be obtained from one or more electronic medical records. Additionally or alternatively, the patient flow data can include operations data associated with the set of medical inpatient units. The operations data can be associated with one or more operational processes associated with the set of medical inpatient units. For instance, the operations data can include status information associated with one or more medical procedures performed within the set of medical inpatient units, time information associated with one or more medical procedures performed within the set of medical inpatient units, statistical information associated with one or more medical procedures performed within the set of medical inpatient units, efficiency information associated with one or more medical procedures performed within the set of medical inpatient units, and/or other information associated with one or more medical procedures performed within the set of medical inpatient units. The operations data can additionally or alternatively include information associated with medical staff within the set of medical inpatient units. For example, the operations data can include status information associated with medical staff within the set of medical inpatient units, time information associated with medical staff within the set of medical inpatient units, location information associated with medical staff within the set of medical inpatient units, statistical information associated with medical staff within the set of medical inpatient units, efficiency information associated with medical staff within the set of medical inpatient units, and/or other information associated with medical staff within the set of medical inpatient units. Additionally or alternatively, the patient flow data can include resource data associated with the set of medical inpatient units. The resource data can be associated with one or more resources utilized within the set of medical inpatient units. For example, the resource data can include medication information utilized within the set of medical inpatient units, medical supplies information utilized within the set of medical inpatient units, medical equipment information utilized within the set of medical inpatient units, and/or other resource information utilized within the set of medical inpatient units. In another embodiment, the patient flow data can provide aggregated information associated with the patient data, the operations data and/or the resource data. Therefore, the patient flow data can provide information associated with patient flow throughout the set of medical inpatient units. For example, the patient flow data can provide real-time patient flow information throughout the set of medical inpatient units.

At 904, the one or more patterns in the patient flow data are monitored, by the system (e.g., by monitoring engine component 106). Additionally or alternatively, the one or more rules associated with the patient flow data 116 can be monitored. Additionally or alternatively, the one or more relationships among the set of medical inpatient units can be monitored. In an embodiment, principles of artificial intelligence can be employed to facilitate monitoring the one or more patterns in the patient flow data and/or generating the one or more abnormalities associated with the one or more patterns in the patient flow data. For example, one or more machine learning techniques can be employed to facilitate monitoring the one or more patterns in the patient flow data and/or generating the one or more abnormalities associated with the one or more patterns in the patient flow data.

At 906, a second machine learning process is performed, by the system (e.g., by monitoring engine component 106), to detect one or more abnormalities associated with the one or more patterns in the patient flow data. The one or more abnormalities associated with the one or more patterns in the patient flow data can be one or more anomalies associated with the one or more patterns in the patient flow data. For instance, the one or more abnormalities associated with the one or more patterns in the patient flow data can be unique behavior and/or unique characteristics associated with the one or more patterns in the patient flow data. In an example, an abnormality associated with the one or more patterns in the patient flow data can be a change or a difference with respect to one or more other predetermined patterns in the patient flow data. In certain embodiments, the one or more patterns in the patient flow data can be compared to one or more other patterns (e.g., one or more predetermined patterns) to facilitate detection of the one or more abnormalities. In an embodiment, the one or more abnormalities associated with the one or more patterns in the patient flow data can predict and/or indicate an event associated with the one or more patterns in the patient flow data. A match between a pattern and another pattern can be, for example, approximately an exact match. Alternatively, a match between a pattern and another pattern can be, for example, a fuzzy match. In certain embodiments, similarity between a pattern and another pattern can be computed based on one or more pattern recognition techniques, one or more statistical techniques, and/or one or more artificial intelligence techniques. In another embodiment, similarity between a pattern and another pattern can be computed based on a distance metric. For example, similarity between a pattern and another pattern can be computed based on a Hamming distance. In another example, similarity between a pattern and another pattern can be computed based on based on a Jaccard distance.

At 908, it is determined whether one or more new patterns are learned. If yes, the methodology 900 returns to 904. If no, the methodology 900 proceeds to 910.

At 910, patient census data associated with a prediction for a total number of patient identities in the set of medical inpatient units during a period of time is determined, by the system (e.g., by patient census component 108), based on the one or more patterns and/or the one or more abnormalities. For example, patient census data can provide a prediction for a total number of patients that will utilize one or more medical inpatient units from the set of medical inpatient units during a future period of time. The patient census data can additionally or alternatively provide one or more predicted emerging patterns in the set of medical inpatient units during the period of time (e.g., the future period of time).

At 912, one or more alerts for a user interface is generated, by the system (e.g., by alert component 110), in response to a determination that the patient census data satisfies a defined criterion. In an embodiment, the one or more alerts can be generated in response to a determination that the patient census data exceeds a defined threshold. For example, the one or more alerts can be generated in response to a determination that the patient census data indicates an extreme census period for one or more medical inpatient units from the set of medical inpatient units. In an embodiment, the one or more alerts can be provided to a display device associated with the user interface such as, for example, a mobile device, a mobile application for a mobile device, a computer, a table computer, a wall display, a monitor and/or another type of display device. In certain embodiments, the one or more alerts can alter a graphical element and/or a graphical indicator for the user interface. For example, the one or more alerts can alter a color of a graphical element associated with the user interface. In certain embodiments, the one or more alerts can provide an indicator associated with one or more emerging census patterns in the set of medical inpatient units. In an embodiment, the patient census data (e.g., the one or more alerts associated with the patient census data) can be outputted in a human interpretable format via a display device associated with the user interface.

At 914, it is determined whether new patient flow data is available. If yes, the methodology 900 returns to 902. If no, the methodology 900 returns to 912. In certain embodiments, the methodology 900 can additionally or alternatively include tuning one or more parameters for a machine learning model associated with the first machine learning process and/or the second machine learning process based on an evaluation of the patient census data.

Figure 10:
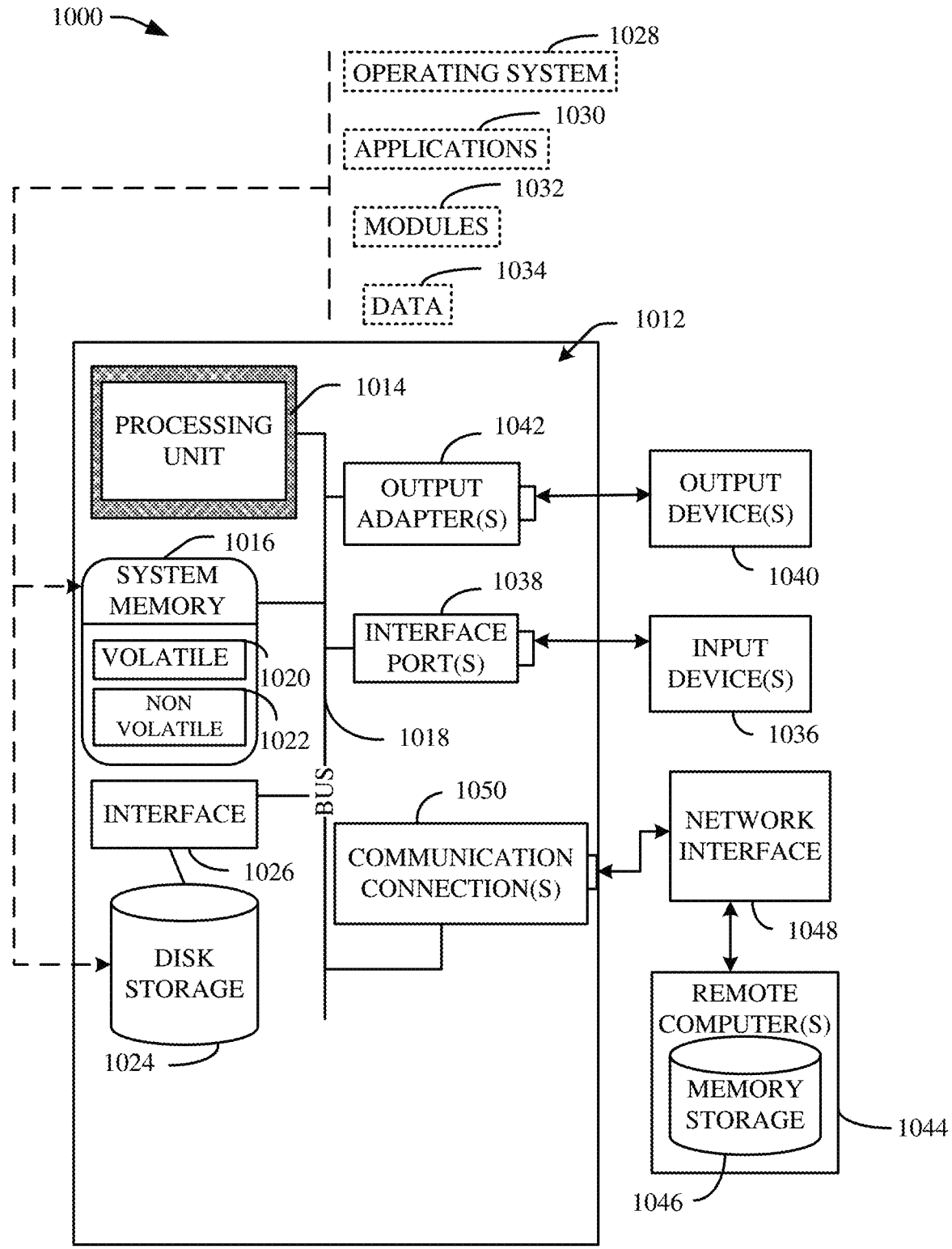
FIG. 10 is a schematic block diagram illustrating a suitable operating environment.
Figure 11:
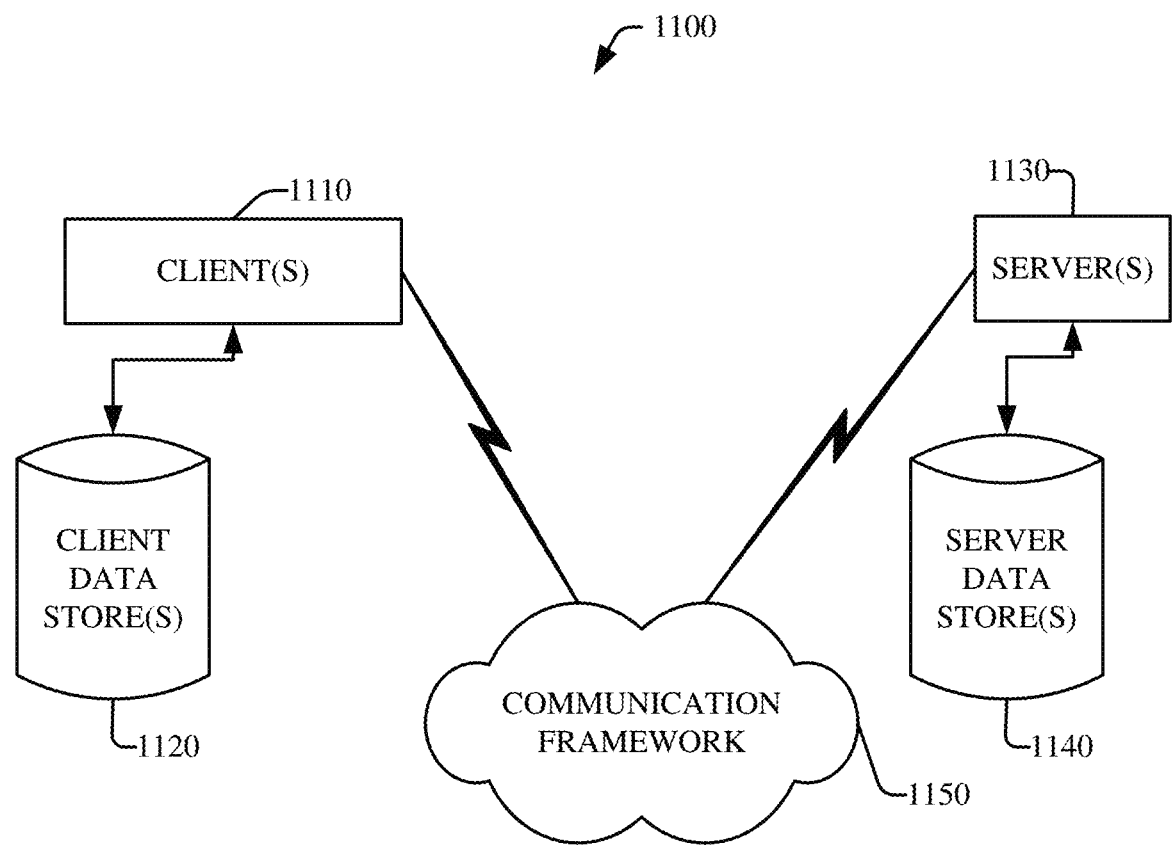
FIG. 11 is a schematic block diagram of a sample-computing environment.

In order to provide a context for the various aspects of the disclosed subject matter, FIGS. 10 and 11 as well as the following discussion are intended to provide a brief, general description of a suitable environment in which the various aspects of the disclosed subject matter may be implemented.

With reference to FIG. 10, a suitable environment 1000 for implementing various aspects of this disclosure includes a computer 1012. The computer 1012 includes a processing unit 1014, a system memory 1016, and a system bus 1018. The system bus 1018 couples system components including, but not limited to, the system memory 1016 to the processing unit 1014. The processing unit 1014 can be any of various available processors. Dual microprocessors and other multiprocessor architectures also can be employed as the processing unit 1014.

The system bus 1018 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1016 includes volatile memory 1020 and nonvolatile memory 1022. The basic input/output system (BIOS), containing the basic routines to transfer information between elements within the computer 1012, such as during start-up, is stored in nonvolatile memory 1022. By way of illustration, and not limitation, nonvolatile memory 1022 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1020 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1012 also includes removable/non-removable, volatile/non-volatile computer storage media. FIG. 10 illustrates, for example, a disk storage 1024. Disk storage 1024 includes, but is not limited to, devices like a magnetic disk drive, floppy disk drive, tape drive, Jaz drive, Zip drive, LS-100 drive, flash memory card, or memory stick. The disk storage 1024 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1024 to the system bus 1018, a removable or non-removable interface is typically used, such as interface 1026.

FIG. 10 also depicts software that acts as an intermediary between users and the basic computer resources described in the suitable operating environment 1000. Such software includes, for example, an operating system 1028. Operating system 1028, which can be stored on disk storage 1024, acts to control and allocate resources of the computer system 1012. System applications 1030 take advantage of the management of resources by operating system 1028 through program modules 1032 and program data 1034, e.g., stored either in system memory 1016 or on disk storage 1024. It is to be appreciated that this disclosure can be implemented with various operating systems or combinations of operating systems.

A user enters commands or information into the computer 1012 through input device(s) 1036. Input devices 1036 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1014 through the system bus 1018 via interface port(s) 1038. Interface port(s) 1038 include, for example, a serial port, a parallel port, a game port, and a universal serial bus (USB). Output device(s) 1040 use some of the same type of ports as input device(s) 1036. Thus, for example, a USB port may be used to provide input to computer 1012, and to output information from computer 1012 to an output device 1040. Output adapter 1042 is provided to illustrate that there are some output devices 1040 like monitors, speakers, and printers, among other output devices 1040, which require special adapters. The output adapters 1042 include, by way of illustration and not limitation, video and sound cards that provide a means of connection between the output device 1040 and the system bus 1018. It should be noted that other devices and/or systems of devices provide both input and output capabilities such as remote computer(s) 1044.

Computer 1012 can operate in a networked environment using logical connections to one or more remote computers, such as remote computer(s) 1044. The remote computer(s) 1044 can be a personal computer, a server, a router, a network PC, a workstation, a microprocessor based appliance, a peer device or other common network node and the like, and typically includes many or all of the elements described relative to computer 1012. For purposes of brevity, only a memory storage device 1046 is illustrated with remote computer(s) 1044. Remote computer(s) 1044 is logically connected to computer 1012 through a network interface 1048 and then physically connected via communication connection 1050. Network interface 1048 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1050 refers to the hardware/software employed to connect the network interface 1048 to the bus 1018. While communication connection 1050 is shown for illustrative clarity inside computer 1012, it can also be external to computer 1012. The hardware/software necessary for connection to the network interface 1048 includes, for exemplary purposes only, internal and external technologies such as, modems including regular telephone grade modems, cable modems and DSL modems, ISDN adapters, and Ethernet cards.

FIG. 11 is a schematic block diagram of a sample-computing environment 1100 with which the subject matter of this disclosure can interact. The system 1100 includes one or more client(s) 1110. The client(s) 1110 can be hardware and/or software (e.g., threads, processes, computing devices). The system 1100 also includes one or more server(s) 1130. Thus, system 1100 can correspond to a two-tier client server model or a multi-tier model (e.g., client, middle tier server, data server), amongst other models. The server(s) 1130 can also be hardware and/or software (e.g., threads, processes, computing devices). The servers 1130 can house threads to perform transformations by employing this disclosure, for example. One possible communication between a client 1110 and a server 1130 may be in the form of a data packet transmitted between two or more computer processes.

The system 1100 includes a communication framework 1150 that can be employed to facilitate communications between the client(s) 1110 and the server(s) 1130. The client(s) 1110 are operatively connected to one or more client data store(s) 1120 that can be employed to store information local to the client(s) 1110. Similarly, the server(s) 1130 are operatively connected to one or more server data store(s) 1140 that can be employed to store information local to the servers 1130.

It is to be noted that aspects or features of this disclosure can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the aspects described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

While the subject matter has been described above in the general context of computer-executable instructions of a computer program that runs on a computer and/or computers, those skilled in the art will recognize that this disclosure also can or may be implemented in combination with other program modules. Generally, program modules include routines, programs, components, data structures, etc. that perform particular tasks and/or implement particular abstract data types. Moreover, those skilled in the art will appreciate that the inventive methods may be practiced with other computer system configurations, including single-processor or multiprocessor computer systems, mini-computing devices, mainframe computers, as well as personal computers, hand-held computing devices (e.g., PDA, phone), microprocessor-based or programmable consumer or industrial electronics, and the like. The illustrated aspects may also be practiced in distributed computing environments where tasks are performed by remote processing devices that are linked through a communications network. However, some, if not all aspects of this disclosure can be practiced on stand-alone computers. In a distributed computing environment, program modules may be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In another example, respective components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

Various aspects or features described herein can be implemented as a method, apparatus, system, or article of manufacture using standard programming or engineering techniques. In addition, various aspects or features disclosed in this disclosure can be realized through program modules that implement at least one or more of the methods disclosed herein, the program modules being stored in a memory and executed by at least a processor. Other combinations of hardware and software or hardware and firmware can enable or implement aspects described herein, including a disclosed method(s). The term "article of manufacture" as used herein can encompass a computer program accessible from any computer-readable device, carrier, or storage media. For example, computer readable storage media can include but are not limited to magnetic storage devices (e.g., hard disk, floppy disk, magnetic strips . . . ), optical discs (e.g., compact disc (CD), digital versatile disc (DVD), blu-ray disc (BD) . . . ), smart cards, and flash memory devices (e.g., card, stick, key drive . . . ), or the like.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or methods herein are intended to include, without being limited to including, these and any other suitable types of memory.

It is to be appreciated and understood that components, as described with regard to a particular system or method, can include the same or similar functionality as respective components (e.g., respectively named components or similarly named components) as described with regard to other systems or methods disclosed herein.

What has been described above includes examples of systems and methods that provide advantages of this disclosure. It is, of course, not possible to describe every conceivable combination of components or methods for purposes of describing this disclosure, but one of ordinary skill in the art may recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A system, comprising:
   a memory that stores computer executable components;
   a processor that executes computer executable components stored in the memory, wherein the computer executable components comprise:
   a data collection component that employs a microservices architecture to collect real-time patient flow data from multiple hospital data sources associated with a hospital and stores the real-time patient flow data in a machine learning database as aggregated patient flow data over time;
   a training component that performs a first machine learning process to learn flow patterns regarding movement of patients between source units of the hospital and inpatient units of the hospital in the aggregated patient flow data and generates different machine learning models for the flow patterns;
   a monitoring engine component that monitors the real-time patient flow data and performs a second machine learning process to detect one or more abnormalities associated with one or more patterns in the real-time patient flow data;
   a patient census component that applies the different machine learning models to the real-time patient flow data to determine patient census data that indicates a total number of forecasted patients to be in respective inpatient units of the inpatient units over one or more future periods of time; and
   an alert component that generates and provides an alert to a device associated with an administrator of the hospital in response to a determination that an emerging pattern in the patient census data is beyond a configured limit for the hospital.

2. The system of claim 1, wherein the multiple hospital data sources are associated with an electronic medical record system, and wherein the real-time patient flow data comprises operations data and resource data.

3. The system of claim 2, wherein the data collection component summarizes the aggregated patient flow data, based on data associated with the patients.

4. The system of claim 2, wherein the data collection component summarizes the aggregated patient flow data based on data associated with the inpatient units.

5. The system of claim 1, wherein the different machine learning models comprise different time period models that respectively predict the total number of forecasted patients to be in the respective inpatient units at different future periods of time over an upcoming forty-hour time frame.

6. The system of claim 1, wherein the training component further tunes one or more parameters different machine learning models based on an evaluation of the patient census data and the one or more abnormalities.

7. The system of claim 1, wherein the patient census component combines outputs of at least some of the different machine learning models using different weights to determine the patient census data.

8. The system of claim 1, wherein the alert component generates a user interface comprising the alert, for display on a display device, that outputs the patient census data in a human interpretable format.

9. A method, comprising:
   employing, by a system comprising a processor, a microservices architecture to collect real-time patient flow data from multiple hospital data sources associated with a hospital;
   storing, by the system, the real-time patient flow data in a machine learning database as aggregated patient flow data over time;
   performing, by the system comprising, a machine learning process to learn flow patterns regarding movement of patients between source units of the hospital and inpatient units of the hospital in the aggregated patient flow data;
   modeling, by the system, the flow patterns using different machine learning models for the flow patterns;
   applying, by the system, the different machine learning models to the real-time patient flow data to determine patient census data that indicates a total number of forecasted patients to be in respective inpatient units of the inpatient units over one or more future periods of time; and
   providing, by the system, an alert to a device associated with an administrator of the hospital in response to a determination that an emerging pattern in the patient census data is beyond a configured limit for the hospital.

10. The method of claim 9, further comprising:
    outputting, by the system, the patient census data in a human interpretable format via a display device associated with the administrator.

11. The method of claim 9, further comprising:
    obtaining, by the system, patient data associated with the real-time patient flow data from one or more medical logs.

12. The method of claim 9, wherein the performing the machine learning process further comprises learning the flow patterns based on operations data associated with status information for one or more medical procedures.

13. The method of claim 9, wherein the performing the machine learning process further comprises learning the flow patterns based on resource data associated with one or more resources utilized in the inpatient units.

14. The method of claim 9, wherein the applying further comprises combining outputs of at least some of the different machine learning models using different weights to determine the patient census data.

15. The method of claim 9, wherein the different machine learning models comprise different time period models that respectively predict the total number of forecasted patients to be in the respective inpatient units at different future periods of time over an upcoming forty-hour time frame.

16. A computer readable storage device comprising instructions that, in response to execution, cause a system comprising a processor to perform operations, comprising:
 employing a microservices architecture to collect real-time patient flow data from multiple data sources associated with a hospital;
 storing the real-time patient flow data in a machine learning database as aggregated patient flow data over time;
 performing a machine learning process to learn flow patterns regarding movement of patients between source units of the hospital and inpatient units of the hospital in the aggregated patient flow data;
 generating different machine learning models for the flow patterns;
 applying the different machine learning models to the real-time patient flow data to determine patient census data that indicates a total number of forecasted patients to be in respective inpatient units of the inpatient units over one or more future periods of time; and
 generating and providing one or more alerts to a device associated with an administrator of the hospital in response to a determination that an emerging pattern in the patient census data is beyond a configured limit for the hospital.

17. The computer readable storage device of claim 16, wherein the machine learning process is a first machine learning process, and wherein the operations further comprise:
 monitoring the real-time patient flow data using a second machine learning process to detect one or more changes in the flow patterns reflected in the real-time patient flow data; and
 generating and providing one or more additional alerts to the device in response to a determination that the one or more changes are beyond a configured threshold.

18. The computer readable storage device of claim 16, wherein the applying further comprises combining outputs of at least some of the different machine learning models using different weights to determine the patient census data.

19. The computer readable storage device of claim 16, wherein the machine learning process is a first machine learning process, and wherein the operations further comprise:
 performing a second machine learning process to detect one or more changes in the flow patterns in the real-time patient flow data; and
 adapting the different machine learning models based on the one or more changes.

20. The computer readable storage device of claim 16, wherein the different machine learning models comprise different time period models that respectively predict the total number of forecasted patients to be in the respective inpatient units at different future periods of time over an upcoming forty-hour time frame.

\* \* \* \* \*